United States Patent
Chung et al.

(10) Patent No.: US 10,280,215 B2
(45) Date of Patent: May 7, 2019

(54) ANTI-C5 ANTIBODIES AND METHODS OF TREATING COMPLEMENT-RELATED DISEASES

(71) Applicant: Seoul National University R&DB FOUNDATION, Seoul (KR)

(72) Inventors: Junho Chung, Seongnam-si (KR); Hyori Kim, Seoul (KR); Hwa Kyoung Lee, Jeollanam-do (KR); Won Jun Yang, Seongnam-si (KR)

(73) Assignee: Seoul National University R&DB FOUNDATION, Seoul (KR)

( * ) Notice: Subject to any disclaimer, the term of this patent is extended or adjusted under 35 U.S.C. 154(b) by 447 days.

(21) Appl. No.: 14/764,885

(22) PCT Filed: Feb. 3, 2014

(86) PCT No.: PCT/KR2014/000920
§ 371 (c)(1),
(2) Date: Jul. 30, 2015

(87) PCT Pub. No.: WO2014/119969
PCT Pub. Date: Aug. 7, 2014

(65) Prior Publication Data
US 2016/0068592 A1 Mar. 10, 2016

Related U.S. Application Data

(60) Provisional application No. 61/759,015, filed on Jan. 31, 2013, provisional application No. 61/862,248, filed on Aug. 5, 2013.

(51) Int. Cl.
*A61K 39/395* (2006.01)
*C07K 16/18* (2006.01)

(52) U.S. Cl.
CPC .......... *C07K 16/18* (2013.01); *C07K 2317/24* (2013.01); *C07K 2317/33* (2013.01); *C07K 2317/34* (2013.01); *C07K 2317/52* (2013.01); *C07K 2317/622* (2013.01); *C07K 2317/76* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 2010/0166748 A1* | 7/2010 | Guild | G01N 33/6893 424/133.1 |
| 2010/0291694 A1* | 11/2010 | Hass | C07K 14/745 436/86 |
| 2011/0060127 A1* | 3/2011 | Lambris | C07K 14/472 530/350 |
| 2012/0225056 A1* | 9/2012 | Rother | C07K 16/18 424/133.1 |
| 2013/0345406 A1 | 12/2013 | Van De Winkel et al. | |
| 2014/0370012 A1* | 12/2014 | Block | C07K 14/5434 424/134.1 |
| 2017/0260260 A1 | 9/2017 | Diefenbach-Streiber et al. | |

FOREIGN PATENT DOCUMENTS

| | | |
|---|---|---|
| JP | 2010-528993 A | 8/2010 |
| JP | 2011-529700 A | 12/2011 |
| WO | 2010/015608 A1 | 2/2010 |

OTHER PUBLICATIONS

Rudikoff et al., Proc Natl Acad Sci USA 79: 1979-1983 (1982). (Year: 1982).*
Colman, Research in Immunology 145: 33-36 (1994). (Year: 1994).*
Kussie et al., J. Immunol.152: 146-152 (1994). (Year: 1994).*
Chen et al.,EMBO J., 14: 2784-2794 (1995). (Year: 1995).*
Giclas, P. C., et al., "Preparation and characterization of monoclonal antibodies against the fifth component of rabbit complement (C5)," J. Immunol. Methods, 1987, v. 105, pp. 201-209.
Popkov, M., et al., "Rabbit Immune Repertoires as Sources for Therapeutic Monoclonal Antibodies: The Impact of Kappa Allotype-correlated Variation in Cysteine Content on Antibody Libraries Selected by Phage Display", J. Molec. Biol., 2003, vol. 325, pp. 325-335.
Rother, R. P. et al.,"Discovery and development of the complement inhibitor eculizumab for the treatment of paroxysmal nocturnal hemoglobinuria", Nature Biotechnol., 2007, vol. 25, pp. 1256-1264.
Laursen, N. S. et al., "Substrate recognition by complement convertases revealed in the C5-cobra venom factor complex," EMBO Journal, Feb. 2011, v. 30, No. 3, pp. 606-616 (publ. online Jan. 2011).
Aleshin, A. E., et al., "Crystal Structure of C5b-6 Suggests Structural Basis for Priming Assembly of the Membrane Attack Complex," J. Biol. Chem., 2012, v. 287, No. 23, pp. 19642-19652.

* cited by examiner

*Primary Examiner* — Phillip Gambel
(74) *Attorney, Agent, or Firm* — John J. Penny, Jr.

(57) ABSTRACT

The present invention relates to an antibody against C5, and a method for preventing and treating complement-related diseases using the antibody, wherein the antibody against C5 is effectively usable in preventing and treating complement-related diseases by inhibiting complement activation.

13 Claims, 15 Drawing Sheets

Specification includes a Sequence Listing.

HRA-06-H2-1

HRA-06-H2-7

HRA-06-H2-18

HRA-06-H1-9-H2-24

A

B

A

B

ANTI-C5 ANTIBODIES AND METHODS OF TREATING COMPLEMENT-RELATED DISEASES

The present application claims priority under 35 U.S.C. § 120 to U.S. Provisional Patent Application Nos. 61/759,015 and 61/862,248, filed on Jan. 31, 2013 and Aug. 5, 2013, respectively, and under 35 U.S.C. § 365 to PCT/KR2014/000920 filed on Feb. 3, 2014, the disclosures of which are incorporated herein by reference.

REFERENCE TO SEQUENCE LISTING SUBMITTED ELECTRONICALLY VIA EFS-WEB

This application contains a sequence listing which is submitted under 37 CFR § 1.821(c) in an electronic form as the text file entitled 113926-29CorrectedSeqList.txt, created on Nov. 20, 2015, the size of which is 92,348 bytes, and the content of which is specifically incorporated by reference into the application.

TECHNICAL FIELD

The present invention relates to an antibody against Complement component 5 (C5), and a method for preventing and treating complement-related diseases using the antibody.

BACKGROUND ART

A complement system plays a first step in innate immunity to most rapidly recognize and destroy an infection source. In addition, the complement system plays an important role in bridging between innate immunity and adaptive immunity by interaction with immune cells. The complement system is activated by a classical pathway, an alternative pathway and a lectin pathway, and then various kinds of complement proteins are activated. The complement proteins activate secretion of inflammatory substances, control an inflammatory response by interaction with immune cells, and effectively eliminate external infection sources by creating materials attacking the infection source, and the like. It is known that since the complement system inhibits an excessive increase in complementary activity by various kinds of complement regulatory proteins, maintains homeostasis, and plays a critical role through various steps of an inflammatory response and an immune response, when complement protein and complement regulatory protein are not properly controlled, various diseases are caused.

When the complement system is activated by the classical pathway, the alternative pathway and the lectin pathway, Complement component 5 (C5) convertase cleaves C5 into C5a and C5b.

C5 is expressed intracellularly as a single pro-C5 peptide of 1676 amino acids consisting of 18 residue signal sequences and an Arg-rich linker sequence (RPRR) between a mature N-terminal β-chain and a C-terminal α-chain. The mature C5 has a molecular weight of about 190 kDa, and consists of two polypeptide chains (α, 115 kDa and β, 75 kDa) which are connected by disulfide bonds. The C5 convertase cleaves C5 between residues 74 and 75 of the alpha chain to release the 74 amino acid C5a peptide and the C5b fragment which are subsequently incorporated into the membrane-attack complex (MAC).

C5a which is anaphylatoxin, directly activates white blood cells and platelets, and functions as a chemotactic factor of a neutrophil. C5b forms a membrane attack complex together with C6, C7, C8 and C9 in a final step of complement activation to induce hemolysis.

When the complement system is over-activated, since abnormal immune response, and damage of normal cells occur, abnormal activity of the complement system is related with autoimmune diseases, complement-related diseases, and the like. A hemolytic blood disease is a complement-related disease occurring when blood cells are not protected from attack of complement proteins due to genetic defects. It has been reported that complement activation is also related with vigorous immune response and tissue destruction reaction that occur in rheumatoid arthritis, transplant, and the like, and materials such as VEGF are released by tissue damage as well as the immune reaction by the complement activation to cause angiogenesis, which leads to elderly-related macular degeneration and diabetic retinopathy.

That is, the complement system plays an important role in maintaining health; however, it potentially causes diseases or contributes to occurrence of diseases. Accordingly, it is preferable to develop a novel antibody, and the like, of a complement system to be used for treating and diagnosing complement-related diseases.

There are provided a composition comprising a complement inhibitor, a method for treating or preventing complement-related diseases, and a use thereof.

SUMMARY OF INVENTION

Technical Problem

The present invention has been made in an effort to provide a complement C5-binding molecule (for example, a C5-binding antibody or antigen-binding fragment thereof), a pharmaceutical composition comprising the molecule, a method for preparing the molecule and the composition, and a method for using the molecule and the composition, and a use of the molecule and the composition.

In addition, the present invention has been made in an effort to provide an antibody specifically binding to C5 protein, or antigen-binding fragment thereof.

Further, the present invention has been made in an effort to provide a nucleic acid comprising a nucleotide sequence encoding a polypeptide comprising a heavy chain variable region having at least 90%, 95%, 97%, 98% or at least 99% sequence identity to any one selected from SEQ ID NOs: 7, 17, 27, 37, 47 or 57.

In addition, the present invention has been made in an effort to provide a nucleic acid comprising a nucleotide sequence encoding a polypeptide comprising a light chain variable region having at least 90%, 95%, 97%, 98% or at least 99% sequence identity to any one selected from SEQ ID NO: 8, 18, 28, 38, 48 or 58.

Further, the present invention has been made in an effort to provide a vector and a host cell comprising the nucleic acid as described above.

In addition, the present invention has been made in an effort to provide a pharmaceutical composition, comprising: at least one C5-binding molecule (for example, a C5-binding antibody or antigen-binding fragment thereof).

Further, the present invention has been made in an effort to provide a method for treating or diagnosing complement-related diseases, using a C5-binding molecule.

In addition, the present invention has been made in an effort to provide a kit for diagnosing complement-related diseases comprising: a C5-binding molecule; and a container.

Further, the present invention has been made in an effort to provide a use of the C5-binding molecule in preparing a medicament for treating complement-related diseases.

Further, the present invention has been made in an effort to provide a use of the C5-binding molecule in treating complement-related diseases.

Solution to Problem

An exemplary embodiment of the present invention provides an antibody specifically binding to C5 protein, or antigen-binding fragment thereof. The antibody of the present invention or the antigen-binding fragment thereof may prevent or treat complement-related diseases by inhibiting complement activation by specific binding to C5 protein.

An "antibody" of the present invention includes whole antibodies and any antigen-binding portion or single chains thereof. A naturally occurring "antibody" is a glycoprotein comprising at least two heavy (H) chains and two light (L) chains inter-connected by disulfide bonds. Each heavy chain consists of a heavy chain variable region ($V_H$) and a heavy chain constant region ($C_H$). The heavy chain constant region consists of three domains, CH1, CH2 and CH3. Each light chain consists of a light chain variable region ($V_L$) and a light chain constant region ($C_L$). The light chain constant region consists of one domain, CL. The VH and VL regions may be further subdivided into regions of hypervariability, referred to as complementarity determining regions (CDR), interspersed with regions that are more conserved, referred to as framework regions (FR). Each VH and VL consists of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

In some exemplary embodiments, the antibody or antigen-binding fragment thereof that specifically binds to the C5 protein according to the present invention specifically binds to the beta chain (β-chain) of C5, more specifically, to an MG4 domain of the C5 beta-chain, and more specifically, based on amino acid sequences of the beta chain, to 332nd to 398th amino acid residue sequences, preferably, 332nd to 378th amino acid residue sequences, and more preferably 332nd to 364th amino acid residue sequences, more preferably 332nd to 348th amino acid residue sequences and/or 350th to 420th, preferably, 369th to 409th, more preferably, 379th to 398th, and more preferably, 386th to 392nd amino acid residue sequences. For example, as C5 protein capable of being bound, amino acid sequences of human C5 protein are represented by SEQ ID NO. 61, amino acid sequences of the beta chain of human C5 protein are represented by SEQ ID NO. 62, and amino acid sequences of MG4 domain of the beta chain of human C5 protein are represented by SEQ ID NO. 63. Interspecific cross-reactivity with other species such as rabbits, rats, monkeys, and the like is also provided.

In some exemplary embodiments, the antibody or antigen-binding fragment thereof that specifically binds to the C5 protein according to the present invention has an affinity constant ($K_A$) of at least $1\times10^7 M^{-1}$, $1\times10^8 M^{-1}$, $1\times10^9 M^{-1}$, $1\times10^{10} M^{-1}$, or $1\times10^{11} M^{-1}$.

In some exemplary embodiments, the antibody or antigen-binding fragment thereof according to the present invention is antibodies bound to the same epitope as antibodies shown in Tables 1 to 6 below or antigen-binding fragment thereof, and has at least 90%, 95%, 97%, 98% or at least 99% sequence identity to corresponding sequences. In addition, antibodies having complement inhibiting activity are also included in the scope of the present invention. In addition, in a case of some modifications that are obvious in heavy chain and light chain constant regions, the modifications within a scope in which the same or similar complement inhibitory activity is provided are included in the scope of the present invention. Further, since each of these antibodies is capable of being bound to C5, nucleotide sequences that encode VH, VL, full length heavy chain sequences, and full length light chain sequences (amino acid sequences and nucleotide sequences that encode the amino acid sequences) may be "mixed and matched" to create other C5-binding antibodies of the present invention.

TABLE 1

| C5 Antibody (HRA-06-H2-1) | |
|---|---|
| HRA-06-H2-1 | SEQ ID NO and Sequence |
| CDRH1<br>CDR1 of Heavy Chain | 1. GFSFSGRYWIQ |
| CDRH2<br>CDR2 of Heavy Chain | 2. SVWPGITGDTNYANWAKG |
| CDRH3<br>CDR3 of Heavy Chain | 3. EPVAWGGGLDL |
| CDRL1<br>CDR1 of Light Chain | 4. QASQSINNQLS |
| CDRL2<br>CDR2 of Light Chain | 5. YASTLAS |
| CDRL3<br>CDR1 of Light Chain | 6. QGSYYSGGWDYG |
| VH<br>Variable region of Heavy Chain | 7. EVQLVESGGGLVQPGGSLRLSCAASGFS<br>FSGRYWIQWVRQAPGKGLEWVASVWPGITGD<br>TNYANWAKGRFTISRDDSKNTLYLQMNSLRA<br>EDTAVYYCAREPVAWGGGLDLWGQGTLVTVS<br>S |
| VL<br>Variable region of Light Chain | 8. DIQMTQSPSSLSASVGDRVTITCQASQS<br>INNQLSWYQQKPGKAPKLLIYYASTLASGYP<br>SRFSGSGSGTDFTLTISSLQPEDFATYYCQG<br>SYYSGGWDYGFGQGTKVEIK |
| Heavy Chain | 9. EVQLVESGGGLVQPGGSLRLSCAASGFS<br>FSGRYWIQWVRQAPGKGLEWVASVWPGITGD<br>TNYANWAKGRFTISRDDSKNTLYLQMNSLRA<br>EDTAVYYCAREPVAWGGGLDLWGQGTLVTVS<br>SASTKGPSVFPLAPCSRSTSESTAALGCLVK<br>DYFPEPVTVSWNSGALTSGVHTFPAVLQSSG<br>LYSLSSVVTVPSSNFGTQTYTCNVDHKPSNT<br>KVDKTVERKCCVECPPCPAPPVAGPSVFLFP<br>PKPKDTLMISRTPEVTCVVVDVSQEDPEVQF<br>NWYVDGVEVHNAKTKPREEQFNSTYRVVSVL<br>TVLHQDWLNGKEYKCKVSNKGLPSSIEKTIS<br>KAKGQPREPQVYTLPPSQEEMTKNQVSLTCL<br>VKGFYPSDIAVEWESNGQPENNYKTTPPVLD<br>SDGSFFLYSRLTVDKSRWQEGNVFSCSVMHE<br>ALHNHYTQKSLSLSLGK |
| Light Chain | 10. DIQMTQSPSSLSASVGDRVTITCQASQ<br>SINNQLSWYQQKPGKAPKLLIYYASTLASGV<br>PSRFSGSGSGTDFTLTISSLQPEDFATYYCQ<br>GSYYSGGWDYGFGQGTKVEIKRTVAAPSVFI<br>FPPSDEQLKSGTASVVCLLNNFYPREAKVQW<br>KVDNALQSGNSQESVTEQDSKDSTYSLSSTL<br>TLSKADYEKHKVYACEVTHQGLSSPVTKSFN<br>RGEC |

TABLE 2

C5 Antibody (HRA-06-H2-7)

| HRA-06-112-7 | SEQ ID NO and Sequence |
|---|---|
| CDRH1 | 11. GFSFSGRYWIQ |
| CDRH2 | 12. SGWPGATGDTNYANWAKG |
| CDRH3 | 13. EPVAWGGGLDL |
| CDRL1 | 14. QASQSINNQLS |
| CDRL2 | 15. YASTLAS |
| CDRL3 | 16. QGSYYSGGWDYG |
| VH | 17. EVQLVESGGGLVQPGGSLRLSCAASGFSFSGRY WIQWVRQAPGKGLEWVASGWPGATGDTNYANWAKGRF TISRDDSKNTLYLQMNSLRAEDTAVYYCAREPVAWGG GLDLWGQGTLVTSS |
| VL | 18. DIQMTQSPSSLSASVGDRVTITCQASQSINNQL SWYQQKPGKAPKLLIYYASTLASGVPSRFSGSGSGTD FTLTISSLQPEDFATYYCQGSYYSGGWDYGFGQGTKV EIK |
| Heavy Chain | 19. EVQLVESGGGLVQPGGSLRLSCAASGFSFSGRY WIQWVRQAPGKGLEWVASGWPGATGDTNYANWAKGRF TISRDDSKNTLYLQMNSLRAEDTAVYYCAREPVAWGG GLDLWGQGTLVTVSSASTKGPSVFPLAPCSRSTSEST AALGCLVKDYFPEPVTVSWNSGALTSGVHTFPAVLQS SGLYSLSSVVTVPSSNFGTQTYTCNVDHKPSNTKVDK TVERKCCVECPPCPAPPVAGPSVFLFPPKPKDTLMIS RTPEVTCVVVDVSQEDPEVQFNWYVDGVEVHNAKTKP REEQFNSTYRVVSVLTVLHQDWLNGKEYKCKVSNKGL PSSIEKTISKAKGQPREPQVYTLPPSQEEMTKNQVSL TCLVKGFYPSDIAVEWESNGQPENNYKTTPPVLDSDG SFFLYSRLTVDKSRWQEGNVFSCSVMHEALHNHYTQK SLSLSLGK |
| Light Chain | 20. DIQMTQSPSSLSASVGDRVTITCQASQSINNQL SWYQQKPGKAPKLLIYYASTLASGVPSRFSGSGSGTD FTLTISSLQPEDFATYYCQGSYYSGGWDYGFGQGTKV EIKRTVAAPSVFIFPPSDEQLKSGTASVVCLLNNFYP REAKVQWKVDNALQSGNSQESVTEQDSKDSTYSLSST LTLSKADYEKHKVYACEVTHQGLSSPVTKSFNRGEC |

C5 Antibody (HRA-06-H2-18)

| HRA-06-H2-18 | SEQ ID NO and Sequence |
|---|---|
| CDRH1 | 21. GFSFSGRYWIQ |
| CDRH2 | 22. SSSLRGTGDTNYANWAKG |
| CDRH3 | 23. EPVAWGGGLDL |
| CDRL1 | 24. QASQSLNNQLS |
| CDRL2 | 25. YASTLAS |
| CDRL3 | 26. QGSYYSGGWDYG |
| VH | 27. EVQLVESGGGLVQPGGSLRLSCAASGFSFSGRYWI QWVRQAPGKGLEWVASSSLRGTGDTNYANWAKGRFTIS RDDSKNTLYLQMNSLRAEDTAVYYCAREPVAWGGGLDL WGQGTLVTSS |
| VL | 28. DIQMTQSPSSLSASVGDRVTITCQASQSINNQLSW YQQKPGKAPKLLIYYASTLASGVPSRFSGSGSGTDFTL TISSLQPEDFATYYCQGSYYSGGWDYGFGQGTKVEIK |
| Heavy Chain | 29. EVQLVESGGGLVQPGGSLRLSCAASGFSFSGRYWI QWVRQAPGKGLEWVASSSLRGTGDTNYANWAKGRFTIS RDDSKNTLYLQMNSLRAEDTAVYYCAREPVAWGGGLDL WGQGTLVTVSSASTKGPSVFPLAPCSRSTSESTAALGC LVKDYFPEPVTVSWNSGALTSGVHTFPAVLQSSGLYSL SSVVTVPSSNFGTQTYTCNVDHKPSNTKVDKTVERKCC VECPPCPAPPVAGPSVFLFPPKPKDTLMISRTPEVTCV VVDVSQEDPEVQFNWYVDGVEVHNAKTKPREEQFNSTY RVVSVLTVLHQDWLNGKEYKCKVSNKGLPSSIEKTISK AKGQPREPQVYTLPPSQEEMTKNQVSLTCLVKGFYPSD IAVEWESNGQPENNYKTTPPVLDSDGSFFLYSRLTVDK SRWQEGNVFSCSVMHEALHNHYTQKSLSLSLGK |
| Light Chain | 30. DIQMTQSPSSLSASVGDRVTITCQASQSINNQLSW YQQKPGKAPKLLIYYASTLASGVPSRFSGSGSGTDFTL TISSLQPEDFATYYCQGSYYSGGWDYGFGQGTKVEIKR TVAAPSVFIFPPSDEQLKSGTASVVCLLNNFYPREAKV QWKVDNALQSGNSQESVTEQDSKDSTYSLSSTLTLSKA DYEKHKVYACEVTHQGLSSPVTKSFNRGEC |

TABLE 4

C5 Antibody (HRA-06-H2-24)

| HRA-06-H2-24 | SEQ ID NO and Sequence |
|---|---|
| CDRH1 | 31. GFSFSGRYWIQ |
| CDRH2 | 32. SVWPGFTGDTNYANWAKG |
| CDRH3 | 33. EPVAWGGGLDL |
| CDRL1 | 34. QASQSINNQLS |
| CDRL2 | 35. YASTLAS |
| CDRL3 | 36. QGSYYSGGWDYG |
| VH | 37. EVQLVESGGGLVQPGGSLRLSCAASGFSFSGRYWIQWVRQ APGKGLEWVASVWPGFTGDTNYANWAKGRFTISRDDSKNTL YLQMNSLRAEDTAVYYCAREPVAWGGGLDLWGQGTLVTSS |
| VL | 38. DIQMTQSPSSLSASVGDRVTITCQASQSINNQLSWYQQKPG KAPKLLIYYASTLASGVPSRFSGSGSGTDFTLTISSLQPEDFAT YYCQGSYYSGGWDYGFGQGTKVEIK |
| Heavy Chain | 39. EVQLVESGGGLVQPGGSLRLSCAASGFSFSGRYWIQWVRQ APGKGLEWVASVWPGFTGDTNYANWAKGRFTISRDDSKNTL YLQMNSLRAEDTAVYYCAREPVAWGGGLDLWGQGTLVTVS SASTKGPSVFPLAPCSRSTSESTAALGCLVKDYFPEPVTVSWN SGALTSGVHTFPAVLQSSGLYSLSSVVTVPSSNFGTQTYTCNV DHKPSNTKVDKTVERKCCVECPPCPAPPVAGPSVFLFPPKPKD TLMISRTPEVTCVVVDVSQEDPEVQFNWYVDGVEVHNAKTK PREEQFNSTYRVVSVLTVLHQDWLNGKEYKCKVSNKGLPSSI EKTISKAKGQPREPQVYTLPPSQEEMTKNQVSLTCLVKGFYPS DIAVEWESNGQPENNYKTTPPVLDSDGSFFLYSRLTVDKSRW QEGNVFSCSVMHEALHNHYTQKSLSLSLGK |
| Light Chain | 40. DIQMTQSPSSLSASVGDRVTITCQASQSINNQLSWYQQKPG KAPKLLIYYASTLASGVPSRFSGSGSGTDFTLTISSLQPEDFAT YYCQGSYYSGGWDYGFGQGTKVEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVTK SFNRGEC |

TABLE 5

C5 Antibody (HRA-06-H1-9-H2-7)

| HRA-06-H1-9-H2-7 | SEQ ID NO and Sequence |
|---|---|
| CDRH1 | 41. GFSLSGRYWIQ |
| CDRH2 | 42. SGWPGATGDTNYANWAKG |
| CDRH3 | 43. EPVAWGGGLDL |
| CDRL1 | 44. QASQSINNQLS |
| CDRL2 | 45. YASTLAS |
| CDRL3 | 46. QGSYYSGGWDYG |
| VH | 47. EVQLVESGGGLVQPGGSLRLSCAASGFSLSGRYWIQWVRQAPGKGLEWVASGWPGATGDTNYANWAKGRFTISRDDSKNTLYLQMNSLRAEDTAVYYCAREPVAWGGGLDLWGQGTLVTVSS |
| VL | 48. DIQMTQSPSSLSASVGDRVTITCQASQSINNQLSWYQQKPGKAPKLLIYYASTLASGVPSRFSGSGSGTDFTLTISSLQPEDFATYYCQGSYYSGGWDYGFGQGTKVEIK |
| Heavy Chain | 49. EVQLVESGGGLVQPGGSLRLSCAASGFSLSGRYWIQWVRQAPGKGLEWVASGWPGATGDTNYANWAKGRFTISRDDSKNTLYLQMNSLRAEDTAVYYCAREPVAWGGGLDLWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| Light Chain | 50. DIQMTQSPSSLSASVGDRVTITCQASQSINNQLSWYQQKPGKAPKLLIYYASTLASGVPSRFSGSGSGTDFTLTISSLQPEDFATYYCQGSYYSGGWDYGFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 6

C5 Antibody (HRA-06-H1-9-H2-24)

| HRA-06-H1-9-H2-24 | SEQ ID NO and Sequence |
|---|---|
| CDRH1 | 51. GFSLSGRYWIQ |
| CDRH2 | 52. SVWPGFTGDTNYANWAKG |
| CDRH3 | 53. EPVAWGGGLDL |
| CDRL1 | 54. QASQSINNQLS |
| CDRL2 | 55. YASTLAS |
| CDRL3 | 56. QGSYYSGGWDYG |
| VH | 57. EVQLVESGGGLVQPGGSLRLSCAASGFSLSGRYWIQWVRQAPGKGLEWVASVWPGFTGDTNYANWAKGRFTISRDDSKNTLYLQMNSLRAEDTAVYYCAREPVAWGGGLDLWGQGTLVTVSS |
| VL | 58. DIQMTQSPSSLSASVGDRVTITCQASQSINNQLSWYQQKPGKAPKLLIYYASTLASGVPSRFSGSGSGTDFTLTISSLQPEDFATYYCQGSYYSGGWDYGFGQGTKVEIK |
| Heavy Chain | 59. EVQLVESGGGLVQPGGSLRLSCAASGFSLSGRYWIQWVRQAPGKGLEWVASVWPGFTGDTNYANWAKGRFTISRDDSKNTLYLQMNSLRAEDTAVYYCAREPVAWGGGLDLWGQGTLVTVSSASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| Light Chain | 60. DIQMTQSPSSLSASVGDRVTITCQASQSINNQLSWYQQKPGKAPKLLIYYASTLASGVPSRFSGSGSGTDFTLTISSLQPEDFATYYCQGSYYSGGWDYGFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

The antibody of the present invention is prepared by using all antibodies comprising amino acids that are identical to antibodies shown in Tables 1 to 6; antibodies having heavy chain variable regions comprising CDR1, CDR2 and CDR3 sequences, and light chain variable regions comprising CDR1, CDR2 and CDR3 sequences, wherein at least one of the CDR sequences has the antibody described in the present invention or specific amino acid sequences based on conservative modifications thereof; antibodies having functional properties of the C5-binding antibody of the present invention; antibodies bound to the same epitope as the antibodies shown in Tables 1 to 6; antibodies having at least one VH and/or VL sequences described in the present invention as a starting material to engineer a modified antibody, and includes all of antibodies having properties which are partially modified from the starting antibody, comprising the above-mentioned antibodies.

In addition, the antibody of the present invention includes those in which modifications have been made to framework residues within VH and/or VL, in order to improve properties of the antibody.

Further, the antibody of the present invention may be a fully human antibody specifically bound to a C5 protein. When compared to chimeric antibodies, and the like, the antibody of the present invention may have further reduced antigenicity when administered to human subjects. A human antibody includes heavy or light chain variable regions or full length heavy or light chains that are the products of or derived from a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence may be identified as such by comparing the amino acid sequence of the human antibody with the amino acid sequences of human germline immunoglobulins and selecting the human germline immunoglobulin sequence that is closest in sequence to the sequence of the human antibody.

In addition, the antibody of the present invention may be a bispecific or a multispecific antibody. The antibody of the present invention or the antigen-binding fragment thereof may be bispecific molecules that are bound to more than two different binding sites or target molecules.

In some exemplary embodiments, the antibody of the present invention may be a monoclonal antibody specifically bound to the C5 protein. For example, the antibody of the present invention may be a human or humanized monoclonal antibody or a chimeric antibody that specifically binds to the C5 protein, and includes a human heavy chain constant region and a human light chain constant region. In addition, the antibody of the present invention may be a single chain antibody, and may be a Fab fragment, a single-chain variable fragment (scFv), and IgG isotype. Preferable IgG isotpes include IgG2, IgG4 and/or IgG2/4. In some exemplary embodiments, the IgG isotype of the present invention is IgG2/4. IgG2/4 hybrid constant region may have a form in which CH1 and a hinge region of IgG2 are fused with CH2 and CH3 regions of IgG4.

The monoclonal antibody may be produced by general methods for producing monoclonal antibodies, and may be expressed and purified by inserting a synthesized antibody gene into a vector for expressing an antibody, preferably, pcDNA, pCI, pCMV, pCEP4, and the like. In addition, the monoclonal antibody may be produced by using viral or carcinogenic transformation of B lymphocytes, or on the basis of sequence of a murine monoclonal antibody produced using a murine system. For example, DNA encoding heavy chain and light chain immunoglobulin may be obtained from murine hybridoma and may contain non-murine immunoglobulin sequences together therewith, by standard molecular biology techniques. In addition, the human monoclonal antibody against C5 may be produced by using transgenic or transchromosomic mice having a part of a human immune system rather than a mouse immune system.

In some exemplary embodiments, the present invention provides an antibody or antigen-binding fragment thereof comprising a framework in which amino acids are substituted into an antibody framework from the respective human VH or VL germline sequences.

In some exemplary embodiments, the antibody or antigen-binding fragment thereof that specifically binds to the C5 protein according to the present invention includes at least one complementarity determining region (CDR) sequence having at least 95% sequence identity to SEQ ID NO: 1, 2, 3, 4, 5, 6, 11, 12, 21, 22, 31, 32, 41, 42, 51 or 52.

In some exemplary embodiments, the antibody or antigen-binding fragment thereof that specifically binds to the C5 protein according to the present invention includes at least one heavy chain complementarity determining region sequence as the same as SEQ ID NO: 1, 2, 3, 11, 12, 21, 22, 31, 32, 41, 42, 51 or 52.

In some exemplary embodiments, the antibody or antigen-binding fragment thereof that specifically binds to the C5 protein according to the present invention includes at least one light chain complementarity determining region sequence as the same as SEQ ID NO: 4, 5, or 6.

In some exemplary embodiments, the antibody or antigen-binding fragment thereof that specifically binds to the C5 protein according to the present invention includes any one heavy chain complementarity determining region 1 (CDR1) selected from SEQ ID NO: 1, 11, 21, 31, 41 or 51, any one heavy chain complementarity determining region 2 (CDR2) selected from SEQ ID NO: 2, 12, 22, 32, 42 or 52, and/or any one heavy chain CDR3 selected from SEQ ID NO: 3, 13, 23, 33, 43 or 53.

In some exemplary embodiments, the antibody or antigen-binding fragment thereof that specifically binds to the C5 protein according to the present invention includes light chain CDR1 of SEQ ID NO: 4, light chain CDR2 of SEQ ID NO: 5, and/or light chain CDR3 of SEQ ID NO: 6.

In some exemplary embodiments, the antibody or antigen-binding fragment thereof that specifically binds to the C5 protein according to the present invention includes any one heavy chain variable region selected from SEQ ID NO: 7, 17, 27, 37, 47 or 57, or includes a heavy chain variable region having at least 90%, 95%, 97%, or at least 99% sequence identity to any one heavy chain variable region selected from SEQ ID NO: 7, 17, 27, 37, 47 or 57.

In some exemplary embodiments, the antibody or antigen-binding fragment thereof that specifically binds to the C5 protein according to the present invention includes a light chain variable region of SEQ ID NO: 8 or includes a light chain variable region having at least 90%, 95%, 97% or at least 99% sequence identity to the light chain variable region of SEQ ID NO: 8.

In some exemplary embodiments, the antibody or antigen-binding fragment thereof that specifically binds to the C5 protein according to the present invention includes any one heavy chain selected from SEQ ID NO: 9, 19, 29, 39, 49 or 59, or includes a heavy chain variable region having at least 90%, 95%, 97%, or at least 99% sequence identity to any one heavy chain selected from SEQ ID NO: 9, 19, 29, 39, 49 or 59.

In some exemplary embodiments, the antibody or antigen-binding fragment thereof that specifically binds to the C5 protein according to the present invention includes a light chain of SEQ ID NO: 10, or includes a light chain having at least 90%, 95%, 97% or at least 99% sequence identity to the light chain of SEQ ID NO: 10.

In some exemplary embodiments, the antibody or antigen-binding fragment thereof that specifically binds to the C5 protein according to the present invention includes those bound to an epitope in the beta chain of the C5 protein of SEQ ID No. 62. In detail, the epitope may correspond to 332nd to 398th amino acid residue sequences, preferably, 332nd to 378th, more preferably, 332nd to 364th, and much more preferably, 332nd to 348th, and/or 350th to 420th, preferably, 369th to 409th, more preferably, 379th to 398th, and much more preferably, 386th to 392nd amino acid residue sequences, based on the beta chain amino acid sequence of the C5 protein.

In addition, the present invention provides a nucleic acid comprising a nucleotide sequence encoding a polypeptide comprising a heavy chain variable region having at least 90%, 95%, 97%, 98% or at least 99% sequence identity to any one selected from SEQ ID NO: 7, 17, 27, 37, 47 or 57.

In some exemplary embodiments, the nucleic acid comprising a nucleotide sequence encoding a polypeptide comprising a heavy chain variable region of the present invention has sequences shown in Table 7 below or has at least 90%, 95%, 97%, 98% or at least 99% sequence identity to any one sequence thereof.

TABLE 7

Nucleotide Sequence Encoding Heavy Chain Variable Region

| Variable region of Heavy chan | SEQ ID NO and Sequence |
|---|---|
| HRA-06-H2-1 | 64. GAG GTG CAG CTG GTG GAG TCT GGC GGC GGA CTG GTG CAG CCT GGC GGA AGC TTG CGG CTG TCC TGC GCC GCC TCC GGA TTC TCC TTC AGT GGC AGG TAC TGG ATA CAA TGG GTG CGG CAG GCC CCT GGC AAG GGC CTC GAG TGG GTG GCC TCT GTG TGG CCT GGT ATT ACT GGT GAC ACT AAC TAC GCG AAC TGG GCG AAA GGC CGG TTC ACC ATC TCC CGG GAC GAC TCC AAG AAC ACC CTG TAC CTG CAG ATG AAC TCC CTG CGG GCC GAG GAC ACC GCC GTG TAC TAC TGC GCC AGA GAA CCT GTT GCC TGG GGT GGC GGC TTG GAC TTG TGG GGC CAG GGC ACA CTA GTG ACC GTG TCC TCC |
| HRA-06-H2-7 | 65. GAG GTG CAG CTG GTG GAG TCT GGC GGC GGA CTG GTG CAG CCT GGC GGA AGC TTG CGG CTG TCC TGC GCC GCC TCC GGA TTC TCC TTC AGT GGC AGG TAC TGG ATA CAA TGG GTG CGG CAG GCC CCT GGC AAG GGC CTC GAG TGG GTG GCC AGT GGT TGG CCG GGG GCG ACT GGT GAC ACT AAC TAC GCG AAC TGG GCG AAA GGC CGG TTC ACC ATC TCC CGG GAC GAC TCC AAG AAC ACC CTG TAC CTG CAG ATG AAC TCC CTG CGG GCC GAG GAC ACC GCC GTG TAC TAC TGC GCC AGA GAA CCT GTT GCC TGG GGT GGC GGC TTG GAC TTG TGG GGC CAG GGC ACA CTA GTG ACC GTG TCC TCC |
| HRA-06-H2-18 | 66. GAG GTG CAG CTG GTG GAG TCT GGC GGC GGA CTG GTG CAG CCT GGC GGA AGC TTG CGG CTG TCC TGC GCC GCC TCC GGA TTC TCC TTC AGT GGC AGG TAC TGG ATA CAA TGG GTG CGG CAG GCC CCT GGC AAG GGC CTC GAG TGG GTG GCC AGT TCT AGT TTG CGG GGG ACT GGT GAC ACT AAC TAC GCG AAC TGG GCG AAA GGC CGG TTC ACC ATC TCC CGG GAC GAC TCC AAG AAC ACC CTG TAC CTG CAG ATG AAC TCC CTG CGG GCC GAG GAC ACC GCC GTG TAC TAC TGC GCC AGA GAA CCT GTT GCC TGG GGT GGC GGC TTG GAC TTG TGG GGC CAG GGC ACA CTA GTG ACC GTG TCC TCC |
| HRA-06-H2-24 | 67. GAG GTG CAG CTG GTG GAG TCT GGC GGC GGA CTG GTG CAG CCT GGC GGA AGC TTG CGG CTG TCC TGC GCC GCC TCC GGA TTC TCC TTC AGT GGC AGG TAC TGG ATA CAA TGG GTG CGG CAG GCC CCT GGC AAG GGC CTC GAG TGG GTG GCC TCG GTG TGG CCG GGG TTT ACT GGT GAC ACT AAC TAC GCG AAC TGG GCG AAA GGC CGG TTC ACC ATC TCC CGG GAC GAC TCC AAG AAC ACC CTG TAC CTG CAG ATG AAC TCC CTG CGG GCC GAG GAC ACC GCC GTG TAC TAC TGC GCC AGA GAA CCT GTT GCC TGG GGT GGC GGC TTG GAC TTG TGG GGC CAG GGC ACA CTA GTG ACC GTG TCC TCC |
| HRA-06-H1-9-H2-7 | 68. GAG GTG CAG CTG GTG GAG TCT GGC GGC GGA CTG GTG CAG CCT GGC GGA AGC TTG CGG CTG TCC TGC GCC GCC TCC GGA TTC TCC CTC AGT GGC AGG TAC TGG ATA CAA TGG GTG CGG CAG GCC CCT GGC AAG GGC CTC GAG TGG GTG GCC AGT GGT TGG CCG GGG GCG ACT GGT GAC ACT AAC TAC GCG AAC TGG GCG AAA GGC CGG TTC ACC ATC TCC CGG GAC GAC TCC AAG AAC ACC CTG TAC CTG CAG ATG AAC TCC CTG CGG GCC GAG GAC ACC GCC GTG TAC TAC TGC GCC AGA GAA CCT GTT GCC TGG GGT GGC GGC TTG GAC TTG TGG GGC CAG GGC ACA CTA GTG ACC GTG TCC TCC |
| HRA-06-H1-9-H2-24 | 69. GAG GTG CAG CTG GTG GAG TCT GGC GGC GGA CTG GTG CAG CCT GGC GGA AGC TTG CGG CTG TCC TGC GCC GCC TCC GGA TTC TCC CTC AGT GGC AGG TAC TGG ATA CAA TGG GTG CGG CAG GCC CCT GGC AAG GGC CTC GAG TGG GTG GCC TCG GTG TGG CCG GGG TTT ACT GGT GAC ACT |

TABLE 7-continued

Nucleotide Sequence Encoding Heavy Chain Variable Region

| Variable region of Heavy chan | SEQ ID NO and Sequence |
|---|---|
| | AAC TAC GCG AAC TGG GCG AAA GGC CGG TTC |
| | ACC ATC TCC CGG GAC GAC TCC AAG AAC ACC |
| | CTG TAC CTG CAG ATG AAC TCC CTG CGG GCC |
| | GAG GAC ACC GCC GTG TAC TAC TGC GCC AGA |
| | GAA CCT GTT GCC TGG GGT GGC GGC TTG GAC |
| | TTG TGG GGC CAG GGC ACA CTA GTG ACC GTG |
| | TCC TCC |

In addition, the present invention provides a nucleic acid comprising a nucleotide sequence encoding a polypeptide comprising a light chain variable region having at least 90%, 95%, 97%, 98% or at least 99% sequence identity to SEQ ID NO: 8. In some exemplary embodiments, the nucleic acid comprising a nucleotide sequence encoding a polypeptide comprising a light chain variable region of the present invention has sequences shown in Table 8 below or has at least 90%, 95%, 97%, 98% or at least 99% sequence identity to any one sequence thereof.

TABLE 8

Nucleotide Sequence Encoding Light Chain Variable Region

| Variable region of Light chain | SEQ ID NO and Sequence |
|---|---|
| | 70. GAC ATC CAG ATG ACC CAG TCC CCC TCC TCG |
| | CTG AGC GCC TCC GTG GGC GAC CGG GTG ACC |
| | ATC ACC TGC CAG GCC AGT CAG AGC ATT AAC |
| | AAC CAA CTA TCC TGG TAT CAG CAG AAG CCT |
| | GGC AAG GCG CCT AAG CTG CTG ATC TAC TAT |
| | GCA TCC ACT CTG GCA TCT GGC GTG CCT TCC |
| | CGG TTC TCC GGA TCC GGC TCC GGC ACC GAC |
| | TTC ACC CTG ACC ATC TCC TCC CTG CAA CCT |
| | GAG GAC TTC GCC ACC TAC TAC TGC CAA GGC |
| | AGT TAT TAT AGT GGT GGT TGG GAC TAT GGT |
| | TTC GGC CAG GGT ACC AAG GTG GAG ATC AAG |

Further, the present invention provides a vector and a host cell comprising the nucleic acid as described above. In one exemplary embodiment, the present invention provides a host cell comprising (1) a recombinant DNA segment encoding the heavy chain of the antibody of the present invention, and (2) a second recombinant DNA segment encoding the light chain of the antibody of the present invention. In another exemplary embodiment, the present invention provides a host cell comprising a recombinant DNA segment encoding each of the heavy chain and the light chain of the antibody of the present invention. In some exemplary embodiment, the antibody or the antigen-binding fragment thereof is a human monoclonal antibody or antigen-binding fragment thereof.

In order to express polynucleotide encoding a C5-binding antibody, chain, or binding fragment thereof, various expression vector may be used, and in order to produce antibodies in mammalian host cells, both of virus-based and non-viral expression vector may be used. Vectors such as pcDNA, pCI, pCMV, pCEP4, and the like, and host cells such as HEK293, CHO, CHO-DG44, and the like, may be used.

The host cell for harboring and expressing the C5-binding antibody may be an eukaryotic cell or a prokaryotic cell. *E. Coli*, preferably, *E. coli* ER2738. HB2151, BL21, and the like, may be included as examples, which are eukaryotic host cells useful for cloning and expressing the polynucleotide of the present invention. Other microbial host cells suitable for being used include *bacillus*, such as *Bacillus subtilis*, and other enteric bacteria, such as *Salmonella, Serratia* and various *Pseudomonas* species. Other microbes, such as yeast, are capable of being employed to express C5-binding polypeptide of the present invention, and insect cells in combination with baculovirus vectors may also be used.

In some preferred exemplary embodiments, mammalian host cells are used to express and produce the C5-binding polypeptide of the present invention. For example, they may be either a hybridoma cell line expressing endogenous immunoglobulin genes or a mammalian cell line harboring an exogenous expression vector. In addition, for example, as any animal or human cell, a number of suitable host cell lines capable of secreting immunoglobulin comprising CHO cell lines, Cos cell lines, HeLa cells, myeloma cell lines, HEK cell lines, transformed B-cells and hybridomas may be used, preferably, HEK293, CHO, CHO-DG44 may be used.

Further, the present invention provides a pharmaceutical composition, comprising: at least one C5-binding molecule (for example, a C5-binding antibody or antigen-binding fragment thereof).

The pharmaceutical composition of the present invention is effective for treating complement-related diseases. The complement-related diseases include all diseases and pathological conditions in which onset of the diseases is related with abnormality of activation of the complement system, for example, complement deficiency. For example, the complement-related diseases include inflammatory diseases and autoimmune diseases, such as rheumatoid arthritis (RA), osteoarthritis, acute respiratory distress syndrome (ARDS), remote tissue injury after ischemia and reperfusion, complement activation during cardiopulmonary bypass surgery, dermatomyositis, pemphigus, lupus nephritis, glomerulonephritis, renal vasculitis, cardiopulmonary by-pass, heart failure-induced coronary endothelial dysfunction, type II membrane-proliferative glomerulonephritis, acute renal failure, antiphospholipid syndrome, macular degeneration, endophthalmitis, new blood vessel disease, allograft transplantation, hyperacute rejection, hemodialysis, chronic obstructive pulmonary disorder (COPD) respiratory distress syndrome, asthma, paroxymal nocturnal hemoglobinuria (PNH) and aspiration pneumonia, but the present invention is not limited thereto.

The composition may additionally contain one or more other therapeutic agents that are suitable for treating or preventing complement-related diseases. Pharmaceutical carriers enhance or stabilize the composition, or facilitate preparation of the composition. Pharmaceutically acceptable carriers include solvents, dispersion media, coating materials, antibacterial and antifungal agents, isotonic and absorption delaying agents, and the like that are physiologically compatible.

The pharmaceutical composition of the present invention may be administered by a variety of methods known in the art. The route and/or mode of administration vary depending upon the desired results. It is preferred that administration may be intravenous, intramuscular, intraperitoneal, or subcutaneous, or administered proximal to the site of the target. In a specific exemplary embodiment, the antibodies of the present invention are formulated so that they can be administered intravitreally into the eye. Depending on the route of administration, active compounds, that is, antibody, bispecific and multispecific molecules, may be coated with a material to protect the compound from the action of acids and other natural conditions that may inactivate the compound.

The composition needs to be sterile and fluid. Proper fluidity may be maintained, for example, by using the coating materials such as lecithin, or by maintaining required particle size in the case of dispersion liquid and by using surfactants. In many cases, it is preferable to include isotonic agents, for example, sugars, polyalcohols such as mannitol or sorbitol, and sodium chloride in the composition. Long-term absorption of the injectable compositions may be brought about by comprising an agent which delays absorption, for example, aluminum monostearate or gelatin in the composition.

The pharmaceutical composition of the present invention may be prepared in accordance with methods well known and routinely practiced in the art. See, e.g., [Remington: The Science and Practice of Pharmacy, Mack Publishing Co., 20th ed., 2000] and [Sustained and Controlled Release Drug Delivery Systems, J. R. Robinson, ed., Marcel Dekker, Inc., New York, 1978]. The pharmaceutical composition is preferably prepared under GMP conditions. Typically, a therapeutically effective dose or efficacious dose of the C5-binding antibody is employed in the pharmaceutical composition of the present invention. The C5-binding antibodies are formulated into pharmaceutically acceptable dosage forms by conventional methods known to those of skill in the art. Dosage regimens are adjusted to provide the optimum desired response (e.g., a therapeutic response).

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends on a variety of pharmacokinetic factors, for example, activity of the particular compositions of the present invention employed, or an ester, a salt or an amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and other factors.

Treatment dosages need to be titrated to optimize safety and efficacy. For systemic administration with an antibody, the dosage ranges from about 0.0001 to 100 mg/kg, and more usually 0.01 to 15 mg/kg, of the host body weight. An exemplary treatment regime entails systemic administration once per every two weeks or once a month or once every 3 to 6 months. For intravitreal administration with an antibody, the dosage ranges from about 0.0001 to about 10 mg. An exemplary treatment regime entails systemic administration once per every two weeks or once a month or once every 3 to 6 months.

In some methods of systemic administration, dosage is adjusted to achieve a plasma antibody concentration of 1-1000 μg/ml and in some methods 25-500 μg/ml. Alternatively, antibody can be administered as a sustained release formulation, in the case in which less frequent administration is required. Dosage and frequency vary depending on the half-life of the antibody in the patient. In prophylactic applications, a relatively low dosage is administered at relatively infrequent intervals over a long period of time.

Further, the present invention provides a method for treating or diagnosing complement-related diseases, using a C5-binding molecule.

The method for treating complement-related diseases using a C5-binding molecule of the present invention includes: administering a therapeutically effective amount of the antibody or antigen-binding fragment thereof or a composition comprising the same. Term "therapeutically effective amount" used in the present invention indicates an amount of the C5-binding molecule of the present invention or an amount of the composition comprising the C5-binding molecule of the present invention which is effective for preventing or treating complement-related diseases.

When the C5-binding molecule or the composition comprising the same is administered in combination with another agent as a therapeutic agent of the present invention, these two materials may be administered sequentially or simultaneously in any order. Suitable agents for combination treatment with C5-binding antibodies include agents known in the art that are able to modulate activities of complement components. For example, the agents include phosphonate esters, polyanionic substances, sulfonyl fluorides, polynucleotides, pimaric acids, several antiinflammatories, and the like. A combination therapy with at least one therapeutic agent, and the like, may be added, and may bring results of synergism.

The present invention includes diagnostic assay determining expression of C5 protein and/or nucleic acid and C5 protein function in biological samples (for example, blood, blood serum, cells, tissue) or from a subject suffering from complement-related diseases or a subject having a risk thereof. In the antibody of the present invention, for example, radioimmunoassay (REA), enzyme-linked immunosorbent assay (ELISA), and radial diffusion assay are usable for detecting a complement cleavage product. Further, a diagnostic assay, a prognostic assay, pharmacological genetic and clinical monitoring may be used to prophylactically treat a subject with the purpose of prognosis (prediction). In addition, the present invention provides a prognosis (prediction) assay for determining whether or not the subject is at the risk of onset of diseases related with regulation abnormality of activation of complement pathway. For example, mutation in the C5 gene may be assayed in a biological sample. By using this assay with the purpose of prognosis or prediction, a subject may be prophylactically treated before the onset of diseases characterized by expression or activity of the C5 protein, nucleic acid or diseases related therewith.

In addition, the present invention provides a kit for diagnosing complement-related diseases comprising: a C5-binding molecule; and a container. The kit for diagnosing of the present invention may include at least any one of the above-mentioned C5-binding molecule. The container may include a solid carrier, and the C5-binding molecule may be bound to the solid carrier, and the solid carrier may be porous or non-porous, flat or non-planar.

Further, the present invention provides a use of the C5-binding molecule in preparing a medicament for treating complement-related diseases. The C5-binding molecule of the present invention for preparing a medicament or the composition comprising the same may be mixed with acceptable carriers, and the like, and may be prepared as a complex medication together with other agents to have a synergistic effect of the active ingredients.

In addition, the present invention provides a use of the C5-binding molecule. The C5-binding molecule for treating complement-related diseases of the present invention may be used with the purpose of treatment, and may be used as a use of a prognosis assay for determining expression of the C5 protein and/or nucleic acid or C5 protein function from a subject suffering from complement-related diseases or a subject having a risk thereof.

The descriptions in the use, the composition, and the treatment method of the present invention are applied as the same as each other unless contradictory.

The C5-binding molecule of the present invention is effective for diagnosing, preventing, and treating complement-related diseases.

DESCRIPTION OF EMBODIMENTS

Figure 1:
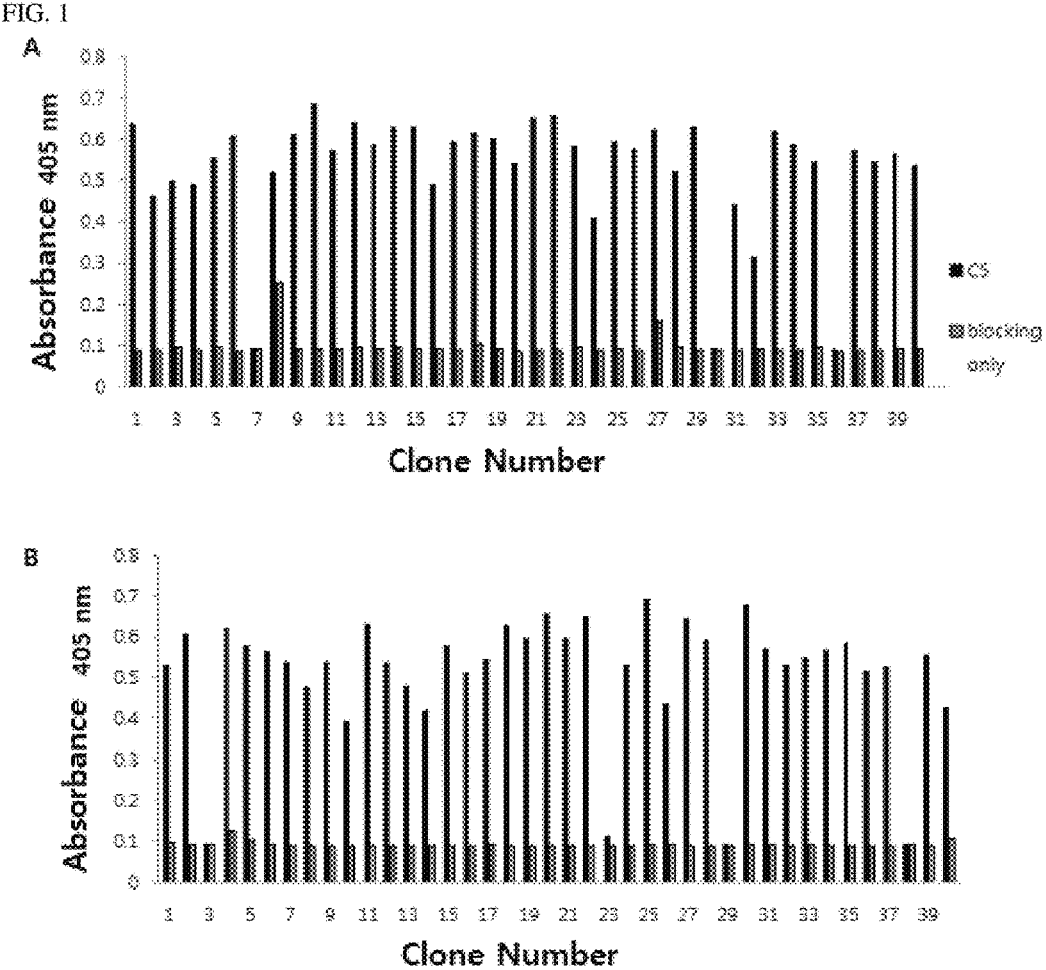
FIG. 1 shows absorbance of 40 clones randomly selected after bio-panning using immune libraries of rabbit (A) and chicken (B) according to an exemplary embodiment of the present invention.

Hereinafter, components and technical features of the present invention are described in more detail through the following examples. However, the following Examples are provided by way of examples, and therefore, the protective scope of the present invention is not limited to only the following Examples.

Various examples described herein are described with reference to the drawings. In the following description, various specific details, for example, specific forms, compositions, and preparation methods, and the like, are described for complete understanding of the present invention. However, specific Examples may be practiced without at least one specific details or together with other known methods and forms. In another exemplary embodiment, known processes and manufacturing techniques are not described as specific details so as not to unnecessarily obscure the present invention. Reference of "one exemplary embodiment" or "Examples" throughout the specification means that specific characteristics, forms, compositions, or properties described associated with Examples are included in one or more Examples of the present invention. Therefore, circumstance of expression "one exemplary embodiment" or "Examples" in various places throughout the specification does not necessarily indicate the same exemplary embodiment of the present invention. In addition, the specific characteristics, forms, compositions, or properties may be combined with each other by any suitable method in at least one exemplary embodiment.

Example 1. Construction of C5 Immune Antibody Library

5 μg of human C5 protein (Calbiochem) was mixed with the RIBI MPL+TDM+CWS adjuvant (Sigma, St. Louis, Mo., USA) and injected subcutaneously into NZW rabbits and chickens, and boost immunizations were performed three times in rabbits and four times in chickens with 2-week intervals. Total RNA was isolated from the spleen and bone marrow of the immune-finished rabbit and spleen, bone marrow and bursa of fabricius of immune-finished chicken, by using TRI reagent (Invitrogen, Carlsbad, Calif., USA), and first-strand cDNA was synthesized using oligo-dT primer and SuperScript™ III First-Strand Synthesis System (Invitrogen). Single-chain Fv libraries were constructed by using primers of Table 9 (rabbit) and Table 10 (chicken) below that are specific to heavy chain variable regions and light chain variable regions of immunoglobulin. For rabbit scFv library, 10 primer combinations of $V_L$ (9λ $V_κ$ and 1×$V_λ$)) and 4 combinations of $V_H$ were used to amplify coding sequences. For chicken scFv library, one primer combination of each $V_λ$ and $V_H$ was used to amplify coding sequences.

TABLE 9

Primers for $V_κ$, $V_λ$ and $V_H$ of rabbit single-chain Fv libraries

| | Vκ 5' Sense Primers |
|---|---|
| RSCVK1 | 71. GGG CCC AGG CGG CCG AGC TCG TGM TGA CCC AGA CTC CA |
| RSCVK2 | 72. GGG CCC AGG CGG CCG AGC TCG ATM TGA CCC AGA CTC CA |
| RSCVK3 | 73. GGG CCC AGG CGG CCG AGC TCG TGA TGA CCC AGA CTG AA |

| | $V_κ$ 3'Reverse Primers, LongLinker |
|---|---|
| RKB9J1o-BL | 74. GGA AGA TCT AGA GGA ACC ACC CCC ACC ACC GCC CGA GCC ACC GCC ACC AGA GGA TAG GAT CTC CAG CTC GGT CCC |
| RKB9Jo-BL | 75. GGA AGA TCT AGA GGA ACC ACC CCC ACC ACC GCC CGA GCC ACC GCC ACC AGA GGA TAG GAT CTC CAG CTC GGT CCC |
| RKB42Jo-BL | 76. GGA AGA TCT AGA GGA ACC ACC CCC ACC ACC GCC CGA GCC ACC GCC ACC AGA GGA TTT GAC SAC CAC CTC GGT CCC |

| | $V_λ$5'Sense Primer |
|---|---|
| RSCλJ | 77. GGG CCC AGG CGG CCG AGC TCG TGC TGA CTC AGT CGC CCT C |

| | $V_λ$3'Reverse Primer, LongLinker |
|---|---|
| RJλo-BL | 78. GGA AGA TCT AGA GGA ACC ACC CCC ACC ACC GCC CGA GCC ACC GCC ACC AGA GGA GCC TGT GAC GGT CAG CTG GGT CCC |

| | $V_H$5'Sense Primers |
|---|---|
| RSCVH1 | 79. GGT GGT TCC TCT AGA TCT TCC CAG TCG GTG GAG GAG TCC RGG |
| RSCVH2 | 80. GGT GGT TCC TCT AGA TCT TCC CAG TCG GTG AAG GAG TCC GAG |
| RSCVH3 | 81. GGT GGT TCC TCT AGA TCT TCC CAG TCG YTG GAG GAG TCC GGG |
| RSCVH4 | 82. GGT GGT TCC TCT AGA TCT TCC CAG SAG CAG CTG RTG GAG TCC GG |

| | $V_H$3'Reverse Primers |
|---|---|
| RSCG-B | 83. CCT GGC CGG CCT GGC CAC TAG TGA CTG AYG GAG CCT TAG GTT GCC C |

| | Overlap Extension Primers |
|---|---|
| RSC-F (sense) | 84. GAG GAG GAG GAG GAG GAG GCG GGG CCC AGG CGG CCG AGC TC |
| RSC-B (reverse) | 85. GAG GAG GAG GAG GAG GAG CCT GGC CGG CCT GGC CAC TAG TG |

TABLE 10

Primers for $V_\lambda$ and $V_H$ of chicken single-chain Fv libraries

$V_\lambda$ Primers

| | | |
|---|---|---|
| CSCVK (sense) | 86. | GTG GCC CAG GCG GCC CTG ACT CAG CCG TCC TCG GTG TC |
| CKJo-B (reverse) | 87. | GGA AGA TCT AGA GGA CTG ACC TAG GAC GGT CAG G |

$V_H$ Primers

| | | |
|---|---|---|
| CSCVHo-FL (sense) | 88. | GGT CAG TCC TCT AGA TCT TCC GGC GGT GGT GGC AGC TCC GGT GGT GGC GGT TCC GCC GTG ACG TTG GAC GAG |
| CSCG-B (reverse) | 89. | CTG GCC GGC CTG GCC ACT AGT GGA GGA GAC GAT GAC TTC GGT CC |

Overlap Extension Primers

| | | |
|---|---|---|
| CSC-F (sense) | 90. | GAG GAG GAG GAG GAG GAG GTG GCC CAG GCG GCC CTG ACT CAG |
| CSC-B (reverse) | 91. | GAG GAG GAG GAG GAG GAG GAG CTG GCC GGC CTG GCC ACT AGT GGA GG |

In each reaction, 1 μl of cDNA was mixed with 60 pmol of each primer, 10 μl of 10× reaction buffer, 8 μl of 2.5 mM dNTPs, 0.5 μl of Taq DNA polymerase and water to a final volume of 100 μl. The PCR reactions were carried out under the following conditions: 30 cycles of 15 sec at 94° C., 30 sec at 56° C., and 90 sec at 72° C., followed by a final extension for 10 min at 72° C. Amplified fragments with length of approximately 350 base pairs were loaded and run on a 1.5% agarose gel, and purified with QIAEX II Gel Extraction Kit (QIAGEN, Valencia, Calif., USA). In the second round of PCR, the first round $V_L$ products and $V_H$ products were randomly joined by overlap extension PCR. Each PCR reaction was performed in a 100 μl mixture composed of 100 ng of purified $V_L$ product and $V_H$ product, 60 pmol of each primer, 10 μl of 10× reaction buffer, 8 μl of 2.5 mM dNTPs and 0.5 μl of Taq DNA polymerase. The PCR reactions were carried out under the following conditions: 20 cycles of 15 sec at 94° C., 30 sec at 56° C., and 2 min at 72° C., followed by a final extension for 10 min at 72° C. About 700 base pair-sized scFv fragments were purified with QIAEX II Gel Extraction Kit (QIAGEN). The scFv fragments and pComb3XSS vector were digested with SfiI restriction enzyme (Roche Molecular Systems, Pleasanton, Calif., USA) by incubating for 8 hr at 50° C. 700 ng of SfiI-digested scFv was ligated with 1400 ng of pComb3X vector using T4 DNA ligase by incubating the reaction mixture for 12 hr at 16° C., followed by ethanol precipitation. Ligated library was transformed into E. coli ER2738 by electroporation. The cells were resuspended with 3 ml of Super Broth (SB) medium and incubated for 1 hr at 37° C. while shaking at 250 rpm. Then 10 ml of SB medium and 3 μl of 100 mg/ml carbenicillin were added to the culture. The library size was determined by plating 0.1, 1 and 10 μl of the culture on Luria Broth (LB) plate containing 50 μg/ml of carbenicillin. After one hour of incubation, 4.5 μl of 100 mg/ml carbenicillin was added to the culture and incubated for an additional hour. The culture was added to 2 ml of VCSM13 helper phage (>$10^{11}$ cfu/ml), 183 ml of SB medium and 92.5 μl of 100 mg/ml carbenicillin and incubated for 2 hr at 37° C. while shaking at 250 rpm. Kanamycin (280 μl) was added to the culture, and the culture was shaken overnight at 250 rpm and 37° C. The next day, the culture was centrifuged at 3,000 g for 15 min. The bacterial pellet was saved for phagemid DNA preparation and the supernatant was transferred to clean centrifuge bottle. 8 g of polyethylene glycol-8000 (PEG-8000, Sigma) and 6 g of NaCl (Merck) were added, and the supernatant was stored on ice for 30 min. The supernatant was centrifuged at 15,000 g for 15 min at 4° C. The phage pellet was resuspended in Tris-buffered saline (TBS) containing 1% bovine serum albumin (BSA).

Example 2: Bio-Panning 3 ug of human C5 antibody was coated with 1×$10^7$ magnetic beads (Dynabeads M270-Epoxy, Invitrogen) at room temperature for 16 hours. The beads were washed with PBS and blocked with PBS containing 3% BSA at room temperature for 1 hour. The coated beads were washed and incubated together with Phage-displayed scFv for 2 hours at room temperature. The beads were washed with 0.5% TPBS to remove phages which were not bound. The bound phages were eluted with 100 ul of 0.1M glycine-HCl and neutralized with 6 ul of 2M Tris-HCl (pH 9.0). The eluted phages infected E. coli ER2738 and were rescued with VCSM13 helper phage for overnight amplification. The input and output phage titer were determined by plating the phage infected bacterial culture at 37° C. on LB plate containing 50 μg/ml of carbenicillin. Next day, phage was precipitated by adding PEG-8000 and NaCl as described in Example 1.

Example 3. Selection of scFv Clones by Phage ELISA

ELISA using phages displaying scFvs was performed against human C5 to analyze the selected clones from bio-panning Microtiter 96-well plate was coated with 100 ng of human C5 per well for overnight at 4° C. and blocked with 3% BSA in PBS. Each phage culture was mixed with an equal volume of 6% BSA in PBS, added to human C5-coated 96-well plate, and incubated for 2 hr at 37° C. After the incubation was finished, the plate was washed and incubated with a HRP conjugated anti-M13 antibody (Amersham, USA). After the incubation was finished, the plate was washed, and 1 µg/ml of 2,2'-azino-bis(3-ethylbenzothiazoline-6-sulphonic acid) (ABTS, Amresco, Ohio, USA) in 0.05 M Citric acid buffer and 1.0% $H_2O_2$ were added to each well, followed by color formation, and the absorbance was measured at 405 nm.

Results thereof were shown in FIG. 1.

FIG. 1A shows immune libraries of rabbit and FIG. 1B shows immune libraries of chicken. As analysis results of gene sequence of clones exhibiting the absorbance of 0.6 or more to human C5, five scFv clones each having different sequence were obtained from two kinds from rabbit immune libraries and three kinds from chicken immune libraries.

In addition, the selected five kinds of scFv clones and eculizumab which is a control, were converted to ScFv-Fc fusion protein to compare binding affinity by ELISA against C5. Amounts of the antibodies bound to C5 were determined by using HRP-bound anti-human IgG according to the same method as described above, and results thereof were shown in FIG. 2.

Figure 2:
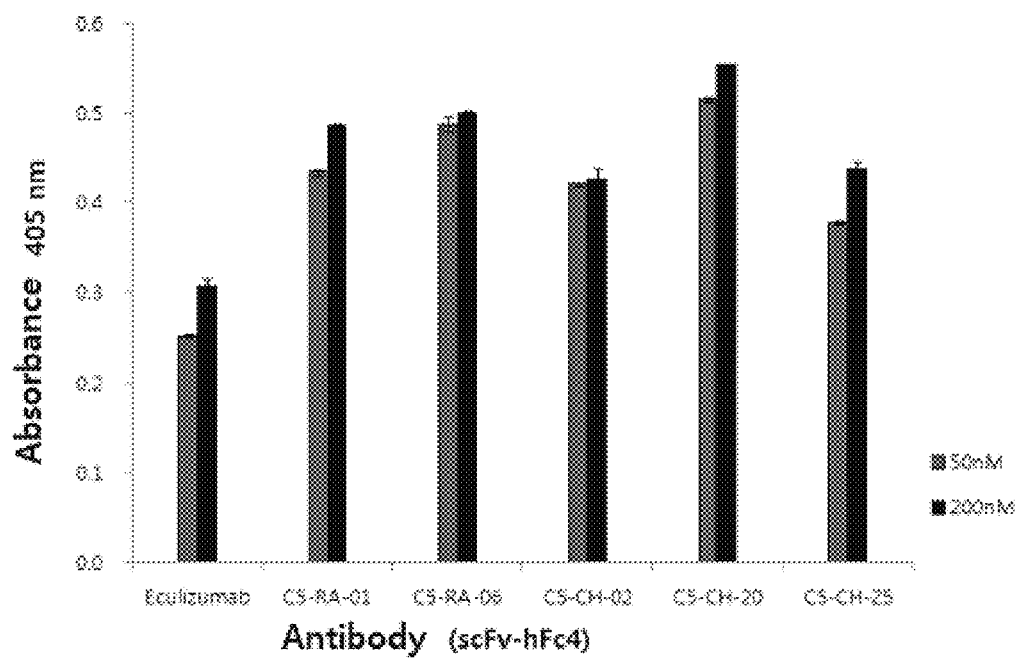
FIG. 2 shows absorbance measurement results of five kinds of antibodies selected from the immune libraries of rabbit and the immune libraries of chicken according to an exemplary embodiment of the present invention, and eculizumab which is a comparative antibody, to human C5.

As shown in FIG. 2, all of the selected five kinds of scFv clones exhibited higher absorbance than that of eculizumab.

Example 4. Construction of Affinity-Matured and Humanized Antibodies

6 CDRs (complementarity determining regions, light chain antigen complementarity determining regions 1-3 [CDRL 1-3], heavy chain antigen complementarity determining regions 1-3 [CDRH1-3]) having binding affinity and activation inhibiting ability to human complement C5 were inserted between 8 framework regions (FRL1-4, FRH1-4) from the human germline Kappa1/IGHV3-23 to synthesize humanized anti-complement C5 scFv gene (HRA-06, Genscript, Piscataway, N.J., USA).

To generate mutant sub-libraries of HRA-06, oligonucleotides containing degenerate codons NNK or MNN (N=A, T, G or C, K=G or T, M=A or C) were used. ScFv gene of HRA-06 was used for template DNA. Randomized codons were introduced in five CDRs except CDRH3 by PCR. Amplified scFv fragments were purified with QIAEX II Gel Extraction Kit (QIAGEN). The scFv and pComb3XSS vector were digested with SfiI restriction enzyme (Roche Molecular Systems) and ligated, followed by ethanol precipitation. Ligated libraries were transfected into *E. coli* ER2738 by the same method as Example 1 to construct phage libraries. Antigens were selected based on the constructed phage libraries by the same method as Example 2. Lastly, binding affinity to C5 was confirmed by phage ELISA according to the same method as Example 3.

Figure 3:
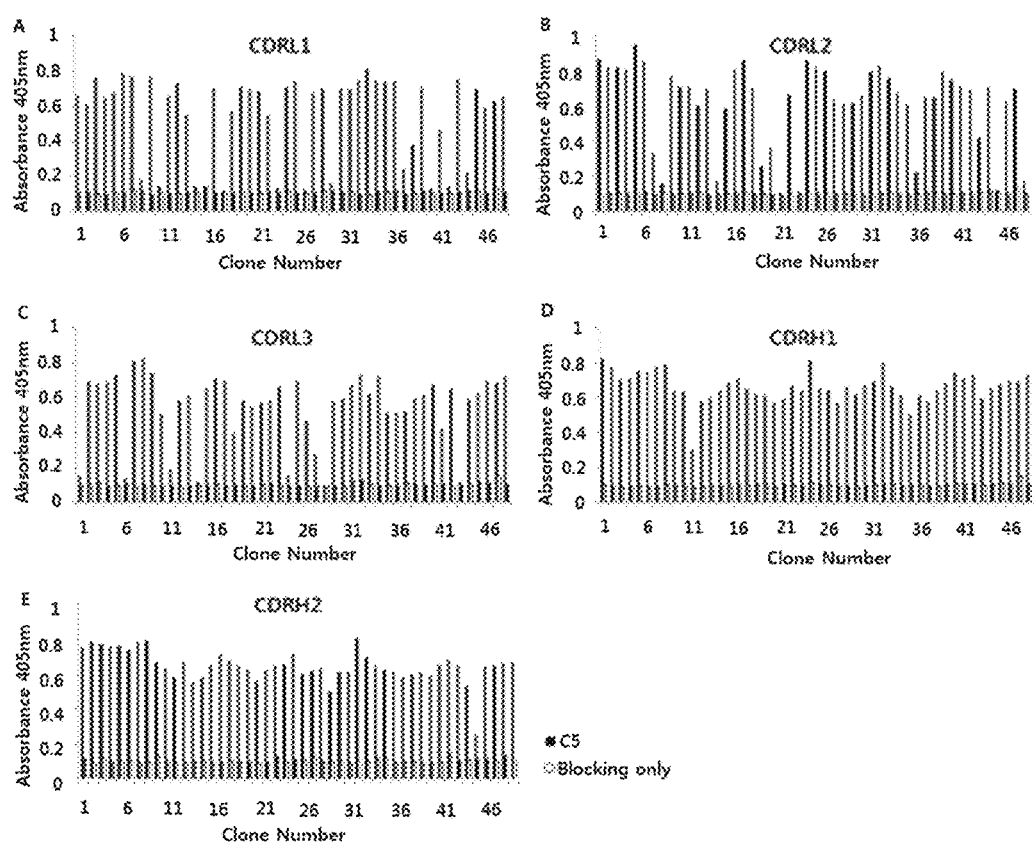
FIG. 3 shows results of a number of clones having binding affinity to C5, obtained from five mutant sub-libraries.

As shown in FIG. 3, a number of clones having binding affinity to C5 were obtained from 5 kinds of mutant sub-libraries.

Example 5. Construction of Recombinant Anti-C5 Antibodies and Eculizumab as a Control 1. Sub-Cloning of Anti-C5 Antibody into Full IgG Vector and scFv-Fc Vector Gene encoding human IgG2 hinge and IgG2/4 hybrid CH2-CH3 was inserted into pCEP4 vector (Invitrogen) by HindIII (New England Biolabs) and XhoI (New England Biolabs) restriction enzyme. The gene encoding anti-C5 scFv was sub-cloned in the 5' end of Fc region by two SfiI restriction sites. For the light chain, human immunoglobulin $C_\kappa$ gene was sub-cloned into a mammalian expression vector. For the heavy chain, the gene from human CH1 and the hinge of human IgG2 to IgG2/4 hybrid CH2-CH3 region was sub-cloned into the mammalian expression vector. Variable light chains and variable heavy chains were sub-cloned into this full IgG vector. Antibody sequence of eculizumab was obtained by synthesizing heavy chain and light chain genes based on antibody sequence stated in examination report of Eculizumab (Product Name: Soliris) posted on 'Japan Pharmaceuticals and Medical Devices Agency (PMDA)'.

2. Transfection and Protein Purification

Transfection was performed to over-express recombinant proteins. 2 µg of mammalian expression vector per ml of culture volume and 4 µg of polyethyleneimine/ml (PEI, Polysciences, Warrington, Pa., USA) were mixed in 150 mM NaCl corresponding to ⅒ of culture volume, and let stand at room temperature for 15 min. The mixture was added to the HEK 293F cells ($2\times10^6$ cells/ml) and incubated for 5 days under the following condition: FreeStyle™ 293 Expression medium containing 100 U/ml penicillin (Invitrogen) and 100 U/ml streptomycin (Invitrogen), 37° C., 7% $CO_2$, 135 rpm on an orbital shaker. Cell culture supernatants were harvested and subjected to protein A affinity gel chromatography to purify IgG and Fc fusion protein.

Example 6. Measurement of Binding Affinity of Monoclonal Antibody

ELISA (enzyme-linked immunosorbent assay) was performed to measure complement C5 binding affinity of the antibodies produced by Example 5. The antibodies diluted for each concentration were added to 96-well plates coated with C5 to perform reaction. Horseradish peroxidase-labeled anti-human IgG antibody was used as a secondary antibody, followed by color formation with ABTS (2,2'-Azinobis[3-ethylbenzothiazoline-6-sulfonic acid]-diammonium salt), and absorbance was measured by the same method as Example 3.

The monoclonal antibodies used in this experiment were six kinds of affinity-matured and humanized anti-C5 antibodies (HRA-06-H2-1, HRA-06-H2-7, HRA-06-H2-18, HRA-06-H2-24, HRA-06-H1-9-H2-7, HRA-06-H1-9-H2-24) and positive control group antibody Eculizumab, and negative control group antibody Palivizumab, and results thereof were shown in FIG. 3.

Figure 4:
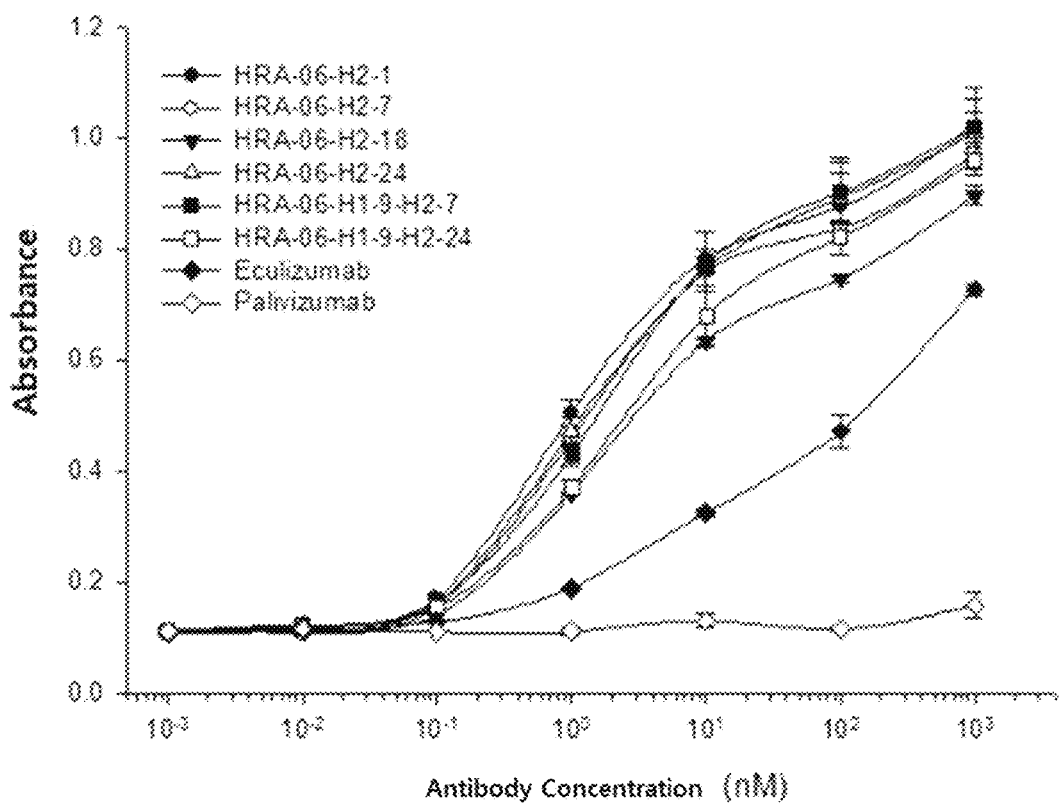
FIG. 4 shows comparison results of binding affinity of clones with improved affinity produced by using HRA-06 clone which is humanized clone according to an exemplary embodiment of the present invention as a template.

As shown in FIG. 4, all of the anti-complement C5 antibodies exhibited binding affinity to C5 and six kinds of affinity-matured and humanized anti-C5 antibodies exhibited high absorbance as compared to Eculizumab.

Example 7: Complement-Dependent Cytotoxicity (CDC) Assay In Vitro

CD20-expressing human Burkitt's lymphoma cell line Ran was kept in RPMI 1640 supplemented with 10% FBS (Invitrogen), 100 U/ml penicillin (Invitrogen) and 100 U/ml streptomycin (Invitrogen). Target cells were washed and resuspended at a concentration of $1\times10^6$ cells/ml. Anti-CD20 human IgG, rituximab (Roche) were diluted with CDC solution at a concentration of 3 µg/ml. Equal volume of target cells and sensitizing antibody were mixed together to make a volume of 100 µl/well in 96-well plate, and let stand at room temperature for 5 min Assay was started by adding human complement serum, resulting in a final volume of 150 µl per well and a final concentration of 4% blood serum. After 2 hours of incubation, 15 µl of Tetrazolium salt (WST-1, Takara Bio, Japan) was added to each well and the plate was incubated for additional 2 hours. The viable cells were analyzed by measuring OD at 450 nm Effect of anti-C5 antibody was evaluated by pre-incubation with serum at 37° C. for 30 min prior to adding to target cells and sensitizing antibody mixture. Same concentration of Palivizumab was used as an IgG control. Percentage of cell viability was calculated with the formula:

% Viability=(Test$_{antibody}$−Background)/
(Test$_{Without\ Antibody}$−Background)×100

Figure 5:
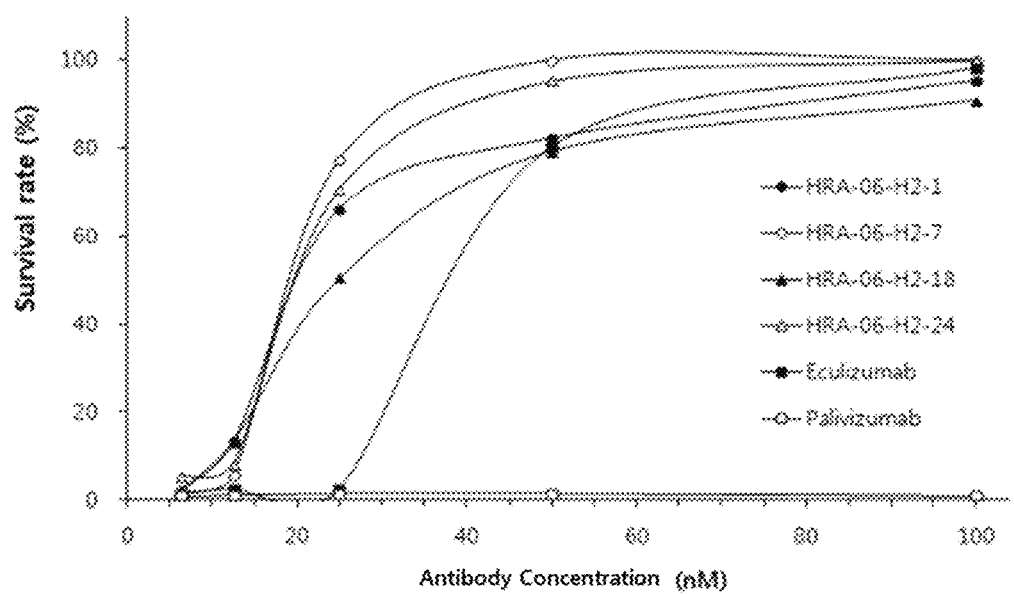
FIG. 5 shows that the antibody produced according to an exemplary embodiment of the present invention has high complement dependent cytotoxicity inhibitory ability in complement dependent cytotoxicity assay.

Results thereof were shown in FIG. 5.

As shown in FIG. 5, the affinity-matured and humanized anti-C5 antibodies produced according to the present invention exhibited CDC inhibitory ability, and all of the antibodies exhibited high cell viability as compared to Eculizumab.

Example 8: Measurement of C5a Production Content In Vitro

After 2 hours of incubation of target cells, sensitizing antibody and serum, the cells were pelleted by centrifugation and the supernatant was assayed for C5a content by sandwich ELISA using the BD OptiEIA™ Human C5a ELISA Kit II (BD Biosciences, San Jose, Calif., USA) following manufacturer's instruction.

Figure 6:
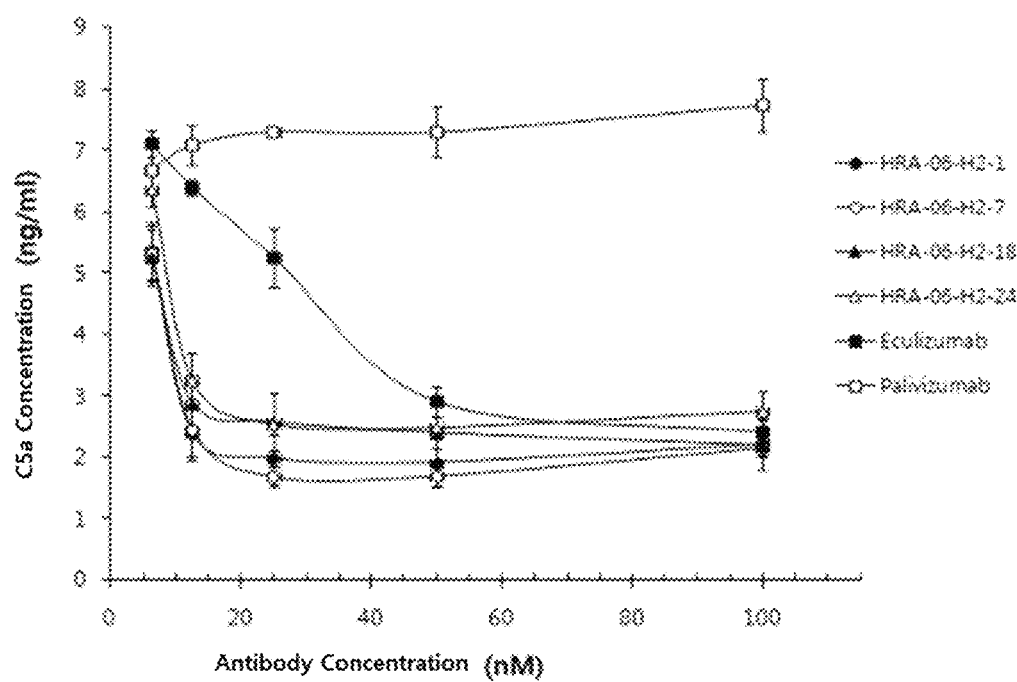
FIG. 6 shows the antibody produced according to an exemplary embodiment of the present invention has high C5a generation inhibitory ability in C5a generation assay.

Results thereof were shown in FIG. 6.

As shown in FIG. 6, all of the affinity-matured and humanized anti-C5 antibodies produced according to the present invention exhibited C5a production inhibitory ability, and all of four kinds of affinity-matured and humanized anti-C5 antibodies exhibited high inhibitory ability as compared to Eculizumab.

Example 9: Measurement of Cross-Species Reactivity of Monoclonal Antibody

Immunoblotting was performed to confirm whether or not the monoclonal antibody was bound to the complement C5 of other species rather than human. Blood serums of human C5 protein and human (Sigma), rhesus monkey, BALB/c mouse, Wistar rat, NZW rabbit were diluted and subjected to SDS-PAGE, respectively, and resolved proteins were transferred to nitrocellulose membrane. Immunoblotting was performed by the anti-complement C5 antibody HRA-06-H2-1 produced according to the present invention.

Figure 7:
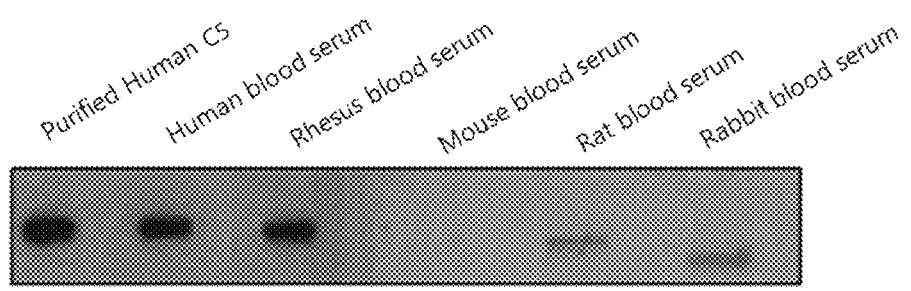
FIG. 7 shows cross-species reactivity of a monoclonal antibody produced according to an exemplary embodiment of the present invention.
Figure 8A:
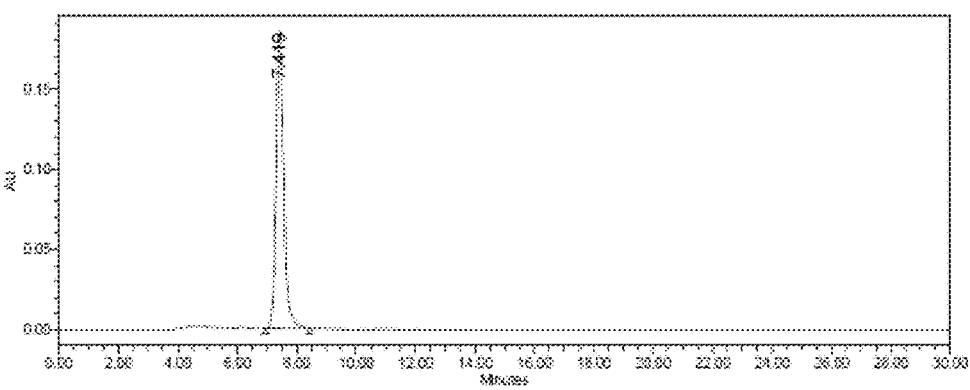
FIG. 8 shows results of antibodies produced and purified according to an exemplary embodiment of the present invention by size-exclusion chromatography.
Figure 8B:
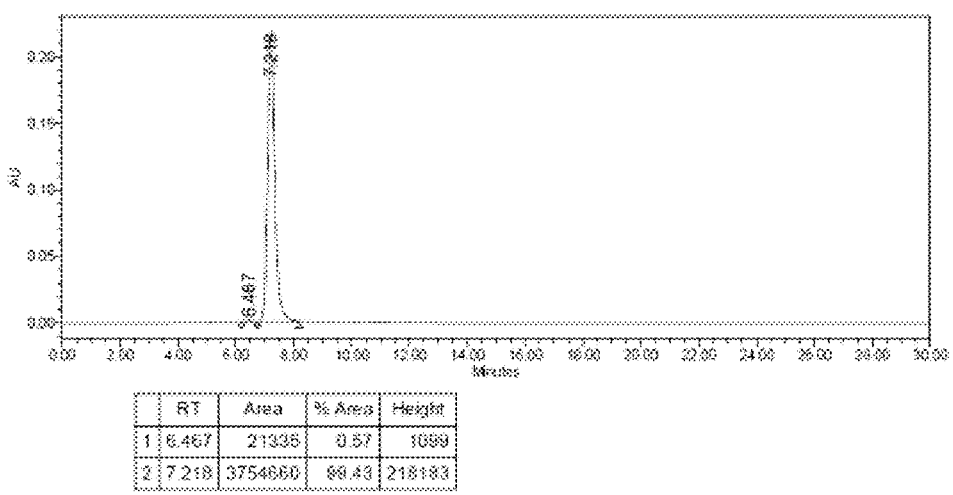
Figure 8C:
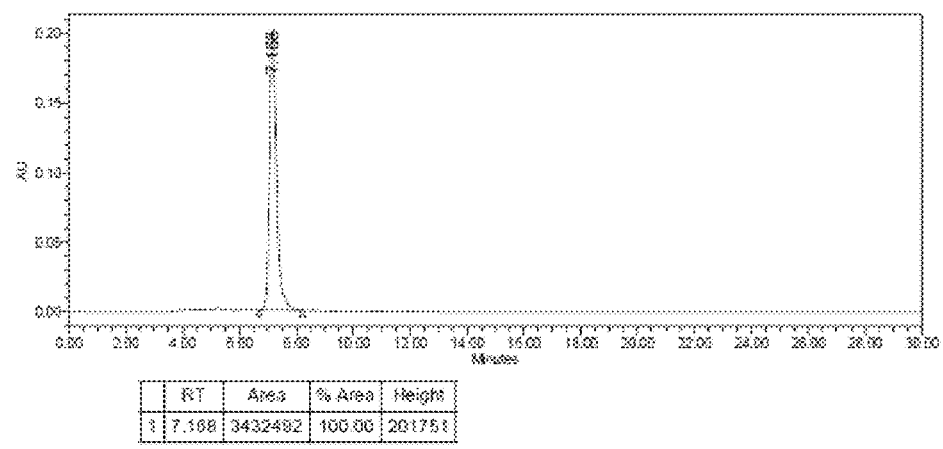
Figure 8D:
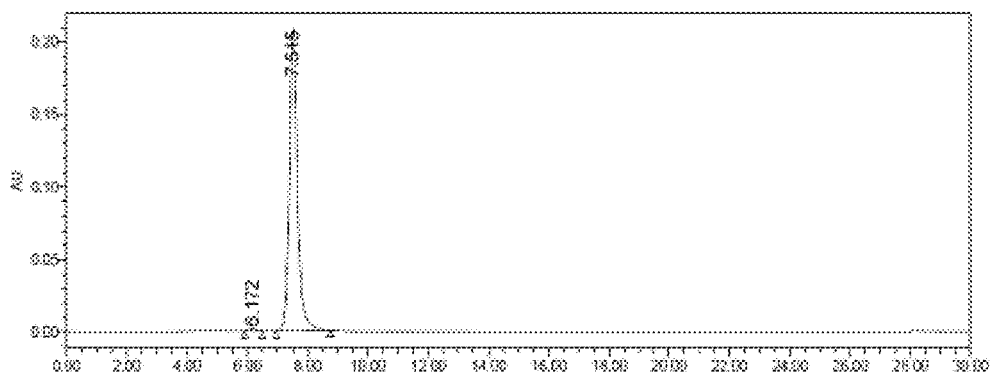
Figure 8E:
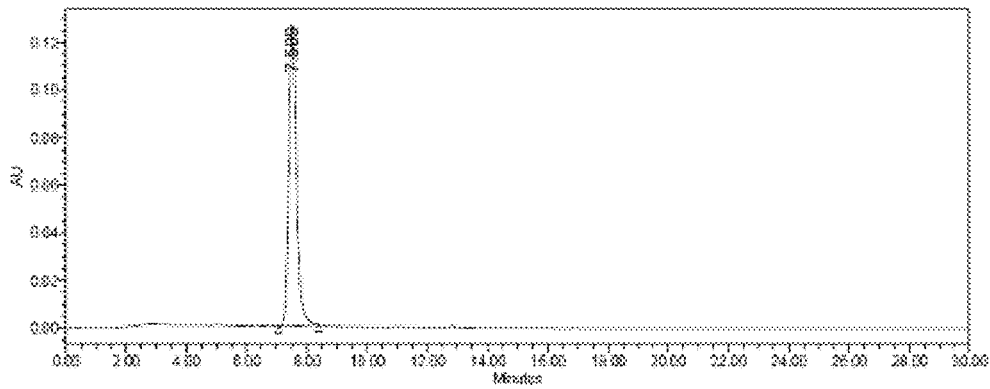
Figure 8F:
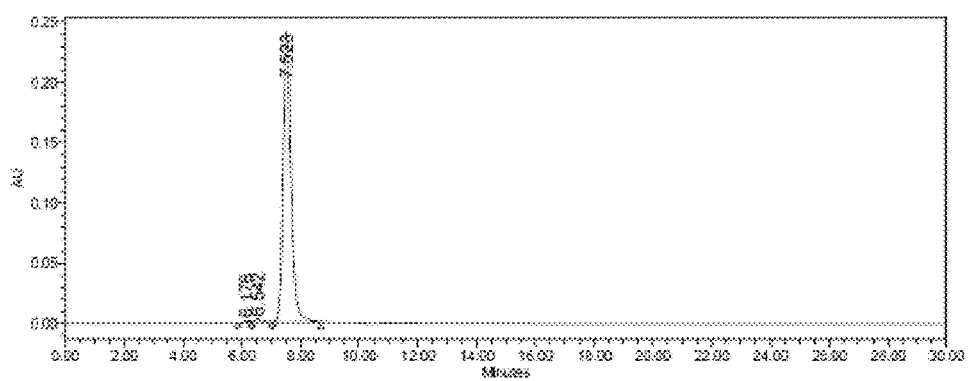

Results thereof were shown in FIG. 7.

As shown in FIG. 7, the anti-complement C5 antibodies exhibited binding affinity to C5 of human (Sigma), rhesus monkey, Wistar rat, and NZW rabbit.

Example 10: Size-Exclusion Chromatography

Size-exclusion chromatography (SEC) analysis was performed on purified antibodies by using Waters 2489 system (Waters Corporation, Milford, Mass., USA), and Zenix-C 300 column (Sepax Technologies, Inc., Newark, Del., USA). Mobile phase composition (150 mM sodium phosphate, pH 7.0) and flow rate (1.0 mL/min) were constant in all runs. Concentration of protein was determined by monitoring the absorbance of column eluate at 280 nm Fractional concentration was calculated by dividing individual peak areas by the sum of peak areas.

Results thereof were shown in FIG. 8. FIGS. 8A to 8D represent A) HRA-06-H2-1, B) HRA-06-H2-7, C) HRA-06-H2-18, D) HRA-06-H2-24, E) HRA-06-H1-9-H2-7 and F) HRA-06-H1-9-H2-24, respectively.

As shown in FIG. 8, it was confirmed that aggregation was hardly detected in physical chemical properties of the anti-complement C5 antibody.

Example 11: Epitope Mapping

1. Confirmation of Binding of Antibody to C5 Beta-Chain

Figure 9:
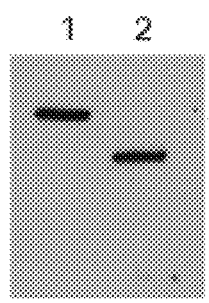
FIG. 9 shows that the antibody according to an exemplary embodiment of the present invention is bound to a beta chain of C5.
Figure 9:
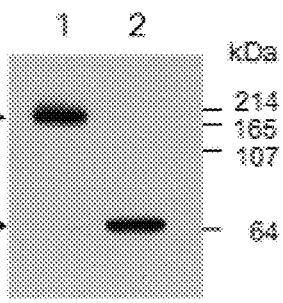

Complement C5 proteins were subjected to SDS-PAGE under non-reducing condition (lane 1) and reducing condition (lane 2), respectively, followed by immunoblotting using the anti-complement C5 antibody, to confirm whether or not beta-chain binding was formed. Results thereof were shown in FIG. 9.

FIG. 9A shows the binding when Eculizumab was used as an antibody, and FIG. 9B shows the binding when HRA-06-H2-1 according to the present invention was used as an antibody. As known in the art, it was confirmed that Eculizumab was bound to C5 (entire complement protein), and bound to alpha-chain in lane 2 under reducing condition. Meanwhile, it was confirmed that HRA-06-H2-1 antibody according to the present invention bound to C5 (entire complement protein), and bound to beta-chain in lane 2 under reducing condition.

2. Production of C5 Beta Chain Mutant Domains as Fc Fusion Proteins and Identification of Binding Site Six domains consisting beta chain of C5 and serial deletion mutant of beta chain were amplified from cDNA. The primers were designed to add SfiI restriction sites at both the 5' and 3' ends (Table 11). The serial deletion mutant of beta chain of C5 was amplified by primer combination as described in Table 12. The amplified PCR fragments were digested with SfiI and cloned into modified pCEP4 vector containing the hinge region and CH2-CH3 domain of human IgG1 at the 3' region of the cloning site. These clones were transfected and Fc fusion proteins were purified as described in Example 5.

TABLE 11

| Primer sequences for amplification of beta chain domains | | |
|---|---|---|
| Forward primers (5'→3') | | |
| MG1_F | 92. | GGCCCAGGCGGCCATGGGCCTTTTGGGAATACTTTG |
| MG2_F | 93. | GGCCCAGGCGGCCAATGGATTTCTCTTCATTCATAC |
| MG3_F | 94. | GGCCCAGGCGGCCCCACATTTTTCTGTCTCAATC |
| MG4_F | 95. | GGCCCAGGCGGCCTCTCCCTACAAACTGAATTTG |
| MG5_F | 96. | GGCCCAGGCGGCCACTGATAACCATAAGGCTTTG |
| Linker_F | 97. | GGCCCAGGCGGCCTCCTGGGTGGCATTAGC |
| Reverse primers (5'→3') | | |
| MG1_R | 98. | GGCCGGCCTGGCCGTCATAGGTTATTGGCATTCT |
| MG2_R | 99. | GGCCGGCCTGGCCCAAGACATATTCTTTAACTTC |
| MG3_R | 100. | GGCCGGCCTGGCCGAGGACATATTTGATGCCAG |
| MG4_R | 101. | GGCCGGCCTGGCCCCAATCAATATAAAGGTAACTTTG |
| MG5_R | 102. | GGCCGGCCTGGCCATCCATTCCAGTTGCCATATTA |
| Linker_R | 103. | GGCCGGCCTGGCCGAGAATTTCTTTACAAGGTTC |

TABLE 12

Primer combinations for construction of beta chain domains and deletion mutant of beta chain

| Domain name | Primer combination |
|---|---|
| MG1 | MG1_F/MG1-R |
| MG2 | MG2_F/MG2-R |
| MG3 | MG3_F/MG3-R |
| MG4 | MG4_F/MG4-R |
| MG5 | MG5_F/MG5-R |
| Linker | Linker_F/Linker-R |
| MG1-2 | MG1_F/MG2-R |
| MG1-3 | MG1_F/MG3-R |
| MG1-4 | MG1_F/MG4-R |
| MG1-5 | MG1_F/MG5-R |

The proteins comprising each domain were subjected to SDS-PAGE, respectively, and immunoblotting was performed by using anti-complement C5 antibody (HRA-06-H2-1). Results thereof were shown in FIGS. 10 and 11.

Figure 10:
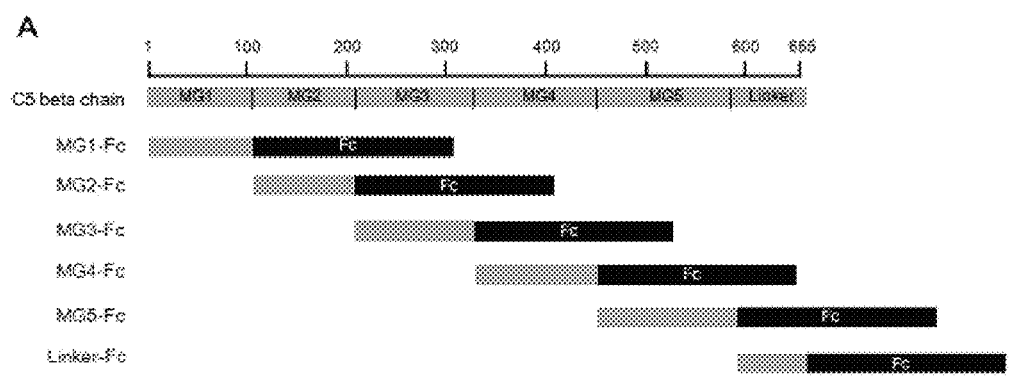
FIG. 10 shows that the antibody according to an exemplary embodiment of the present invention is bound to an MG4 domain of the beta chain of C5.
Figure 10:
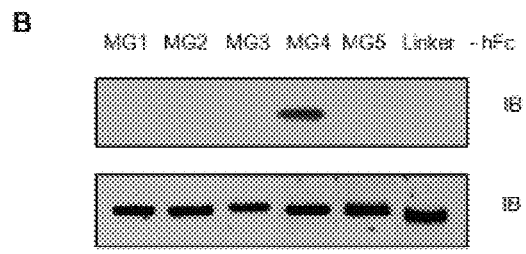

FIG. 10A is schematic diagram showing a structure of the C5 beta chain, and the produced Fc fusion protein, and FIG. 10B shows immunoblotting results. As shown in FIG. 10, it was confirmed that the HRA-06-H2-1 antibody produced according to the present invention bound to the Fc fusion protein having an MG4 domain.

Figure 11:
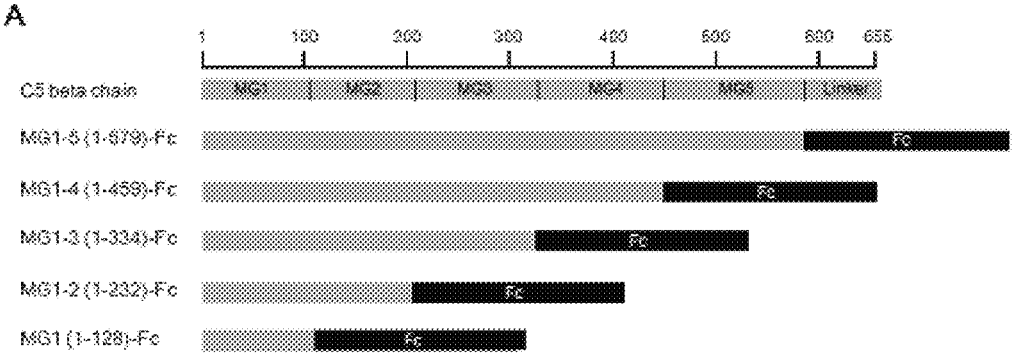
FIG. 11 shows that the antibody according to an exemplary embodiment of the present invention specifically binds to the MG4 domain in a mutant Fc fusion protein in which one domain is sequentially removed from C terminus of the beta chain.
Figure 11:
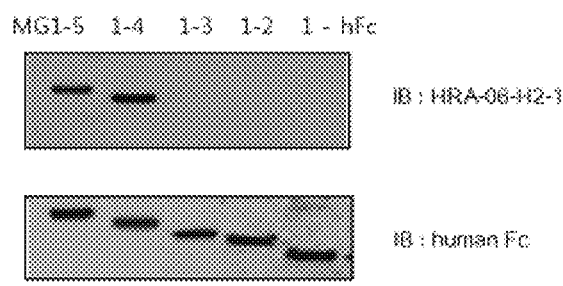

FIG. 11A is schematic diagram showing a structure of the C5 beta chain, and the produced Fc fusion protein, and FIG. 11B shows immunoblotting results. As shown in FIG. 11, it was confirmed that the HRA-06-H2-1 antibody produced according to the present invention was bound only to the Fc fusion protein comprising an MG4 domain.

3. Production of MG4 Domains as Fc Fusion Proteins and Identification of Binding Site MG4 domain of the beta chain and five mutants from which the MG4 domain is sequentially removed from N-terminus of the MG4 domain were cloned. The primers were designed to add SfiI restriction sites at both the 5' and 3' ends (Table 13). The amplified PCR fragments were digested with SfiI and cloned into modified pCEP4 vector containing the hinge region and CH2-CH3 domain of human IgG1 at the 3' region of the cloning site. These clones were transfected and Fc fusion proteins were purified as described in Example 5. The purified Fc fusion proteins were subjected to SDS-PAGE, and immunoblotting was performed as described above.

TABLE 13

Primer sequences for amplification of MG4 domains

Forward primers (5'→3')

| | | |
|---|---|---|
| hMG4_F | 104. | GGCCCAGGCGGCCTCTCCCTACAAACTGAATTTG |
| d332-348_F | 105. | GGCCCAGGCGGCCATTCCATATCCCATCAAGG |
| d332-378_F | 106. | GGCCCAGGCGGCCGTAAACCAAGAGACATCTGAC |
| d332-396_F | 107. | GGCCCAGGCGGCCGATGGAGTAGCTTCCTTTG |
| d332-424_F | 108. | GGCCCAGGCGGCCCCAGAAGAAAATCAGGCC |

Reverse primers (5'→3')

| | | |
|---|---|---|
| hMG4_R | 109. | GGCCGGCCTGGCCCCAATCAATATAAAGGTAACTTTG |

Figure 12:
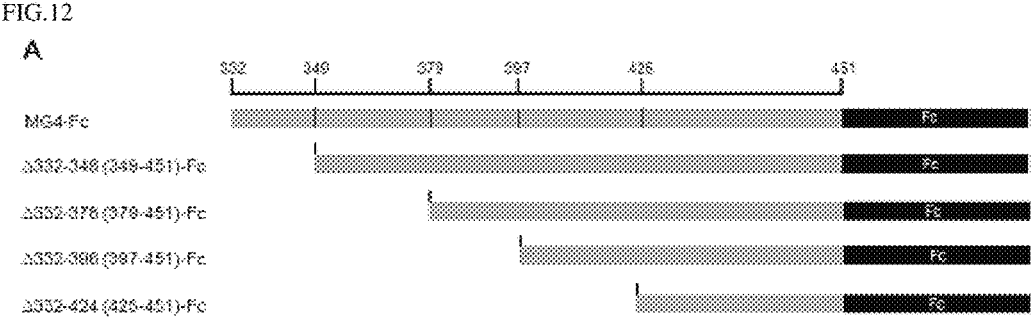
FIG. 12 shows that the antibody according to an exemplary embodiment of the present invention is bound to 332nd to 348th amino acid residues at N-terminus of the beta chain in the mutant from which the MG4 domain is sequentially removed, as confirmed by immunoblotting.
Figure 12:
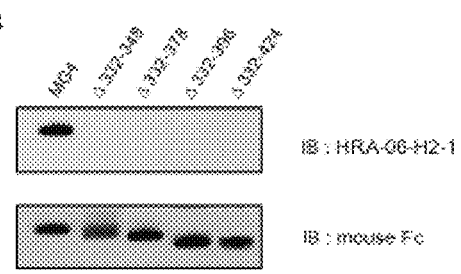

Results thereof were shown in FIG. 12. FIG. 12A shows MG4 domain and Fc fusion protein produced by sequentially removing the domain, and FIG. 12B shows results of immunoblotting, using HRA-06-H2-1 antibody. As shown in FIG. 12, it was confirmed that the binding was not achieved in the mutants from which 332nd-348th amino acid residue sequences were removed from N-terminus of the beta chain, which could be appreciated that 332nd-348th amino acid residue sequences in the MG4 domain of the beta chain were sequences having high antibody-binding possibility.

4. Confirmation of Antibody-Binding Sites from Human/Mouse Hybrid MG4 Domains

Human/mouse hybrid MG4 domains of the C5 beta chain were produced in overlap extension PCR. The primers were designed to add SfiI restriction sites at both the 5' and 3' ends (Table 14). PCR fragments were digested with SfiI and cloned into Sfi I-digested pComb3X vector. These clones were transfected into *E. coli* ER 2738. Single colony from each human/mouse MG4 hybrid was incubated until absorbance at 600 nm reached about 1.0. Phage infection was performed by adding VCSM13 helper phage ($10^{11}$ pfu/ml), followed by incubation at 37° C. for 2 hr. Kanamycin (25 μg/ml) was added and the culture was incubated at 37° C. overnight with constant shaking. Bacteria were removed by centrifugation at 3,000 g for 15 min

TABLE 14

| Primer sequences for amplification of human/mouse hybrid MG4 domains | |
|---|---|
| hMG4-m332-348 Structure | |
| m332-348_F | 110. GGCCCAGGCGGCCTCTCCCTACACACTGAATTTGGTCGCTACTCCTCTTTTCGTGAAGCCCGGGATTCCATATCCCATCAAGGTGC |
| hMG4_R | 111. GGCCCAGGCGGCCTCTCCCTACAAACTGAATTTG |
| Amplification of N-terminus of Mouse MG4 Forward primers (5'→3') | |
| mMG4_F | 112. TCTCCCTACACACTGAATTTGG |
| Reverse primers (5'→3') | |
| m332-359_R | 113. GTCAAGCGAATCTTTAACCTGTGCCTTG |
| m332-368_R | 114. TGTTACTGGGACCCCTCCTACCGCCTG |
| m332-378_R | 115. TTGGTTTACATCGACTGTTTGTGCCATC |
| m332-385_R | 116. TGGATCCAAGTCAGATGTCTCTTGATTCAC |
| m332-392_R | 117. AACACGTGTGATGCTCCTCTTTGTTTCC |
| m332-398_R | 118. GGAAGCTACTCCATCAGTGTCATGAGTG |
| m332-409_R | 119. CACCGTCACATTTGATGGGAGGTTCAGC |
| Amplification of C-terminus of Human MG4 Forward primers (5'→3') | |
| m332-359_F | 120. GTTAAAGATTCGCTTGACCAGTTGGTAG |
| m332-368_F | 121. GGAGGGGTCCCAGTAACACTGAATGCAC |
| m332-378_F | 122. ACAGTCGATGTAAACCAAGAGACATCTGAC |
| m332-385_F | 123. ACATCTGACTTGGATCCAAGCAAAAGTGT |
| m332-392_F | 124. AGGAGCATCACACGTGTTGATGATGGAGTA |
| m332-398_F | 125. ACTGATGGAGTAGCTTCCTTTGTGCTTAATC |

TABLE 14-continued

Primer sequences for amplification of
human/mouse hybrid MG4 domains

| m332-409_F | 126. CCATCAAATGTGACGGTGCTGGAGTTTA |
|---|---|

Reverse primers (5'→3')

| hMG4_R | 127. GGCCCAGGCGGCCTCTCCCTACAAACTGAATTTG |
|---|---| mMG4-h332-348 Structure

| h332-348_F | 128. GGCCCAGGCGGCCTCTCCCTACAAACTGAATTT GGTTGCTACTCCTCTTTTCCTGAAGCCTGGGATTCCA TTTTCCATCAAG |
|---|---|
| mMG4_R | 129. CCAAGCGATGTAAATGTAAC |

Amplification of N-terminus of Human MG4
Forward primers (5'→3')

| hMG4_F | 130. GGCCCAGGCGGCCTCTCCCTACAAACTGAATTTG |
|---|---|

Reverse primers (5'→3')

| h332-359_R | 131. CTCGAGTGAATCTTTAACCTGCACCTTGA |
|---|---|
| h332-368_R | 132. AGTTACTGGGACTCCTCCTACCAACTG |
| h332-378_R | 133. TTGATTCACATCAATTGTTTGTGCATTCAG |
| h332-385_R | 134. TGTTTCCAAGTCAGATGTCTCTTGGTTTAC |
| h332-392_R | 135. GTCATGAGTTACACTTTTGCTTGGATCCA |
| h332-398_R | 136. CACAGCTACTCCATCATCAACACGTGTTAC |
| h332-409_R | 137. CACCGTCACTCCAGATGGGAGATTAAGCAC |

Amplification of C-terminus of Mouse MG4
Forward primers (5'→3')

| h332-359_F | 138. GTTAAAGATTCACTCGAGCAGGCGGT |
|---|---|
| h332-368_F | 139. GGAGGAGTCCCAGTAACTCTGATGGCAC |
| h332-378_F | 140. ACAATTGATGTGAATCAAGAGACATCTGAC |
| h332-385_F | 141. ACATCTGACTTGGAAACAAAGAGGAGCATC |

TABLE 14-continued

Primer sequences for amplification of
human/mouse hybrid MG4 domains

| h332-392_F | 142. CAAAAGTGTAACTCATGACACTGATGGAG |
|---|---|
| h332-398_F | 143. GATGATGGAGTAGCTGTGTTTGTGCTGAAC |
| h332-409_F | 144. CCATCTGGAGTGACGGTGCTAAAGTTTG |

Reverse primers (5'→3')

| mMG4_R | 145. CCAAGCGATGTAAATGTAAC |
|---|---|

Phage ELISA was performed as follows. Anti-C5 IgG2/4, HRA-06-H2-7, was diluted in 0.1 M sodium bicarbonate buffer (pH 8.6) and 100 ng of the antibody was coated on 96 well plate at 4° C. overnight. Each well was blocked by adding 100 µl of 5% skim milk in TBS containing 0.05% Tween 20 and incubated for 1 hr at 37° C. Phage was diluted two fold in 6% BSA/PBS then 50 µl of diluted phage was added to each well, and incubated for 2 hr at 37° C. The plate was washed, and 50 µl of diluted HRP-bound anti-M13 antibody (1:5000) was added, and the plate was incubated for 1 hr at 37° C. The plate was washed, and 50 µl of ABTS substrate solution was added to each well and the absorbance was measured at 405 nm.

Figure 13:
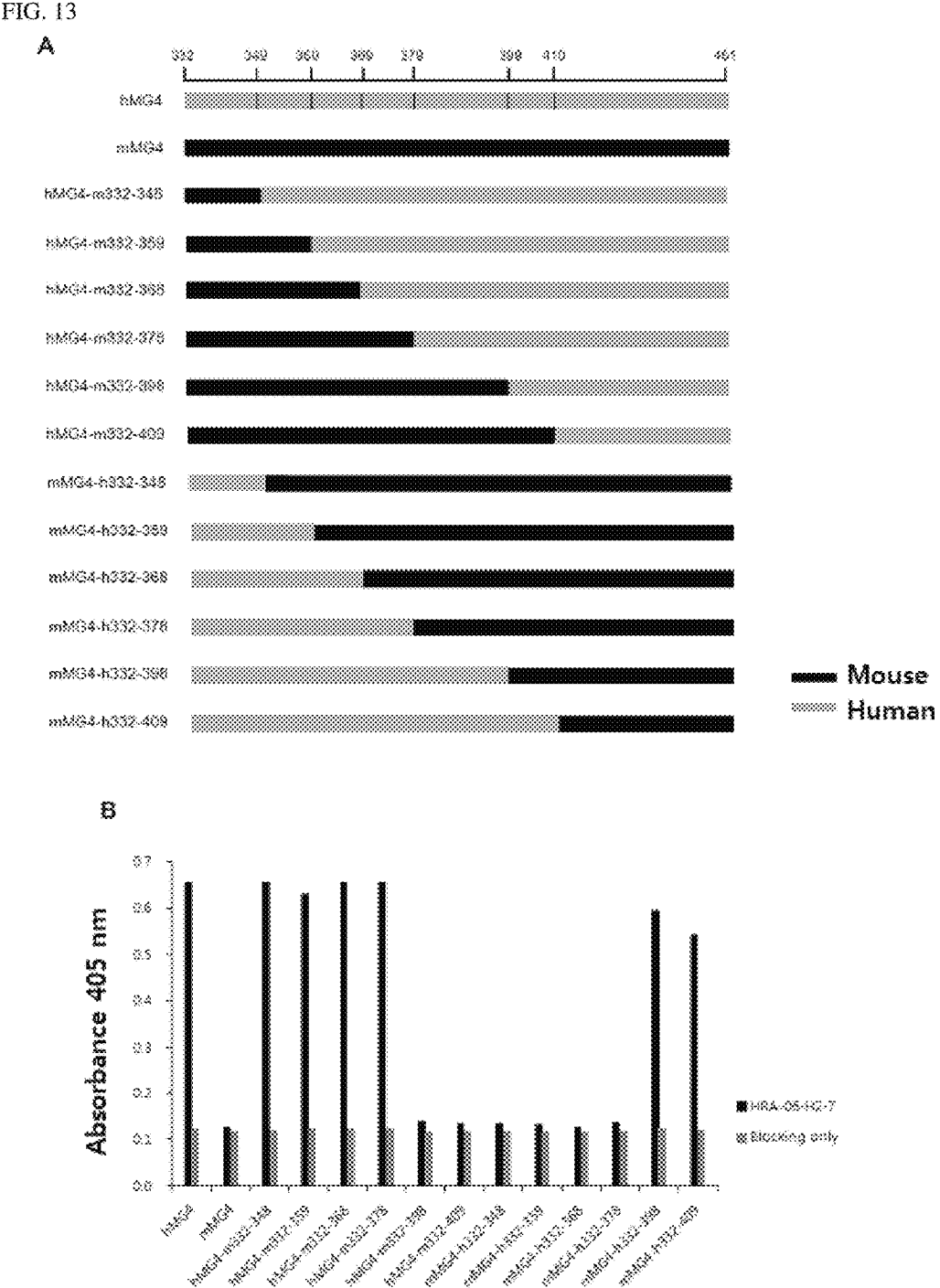
FIG. 13 shows that the antibody according to an exemplary embodiment of the present invention is bound to 379th to 398th amino acid residues at N-terminus of the beta chain, as confirmed by ELISA.
Figure 14:
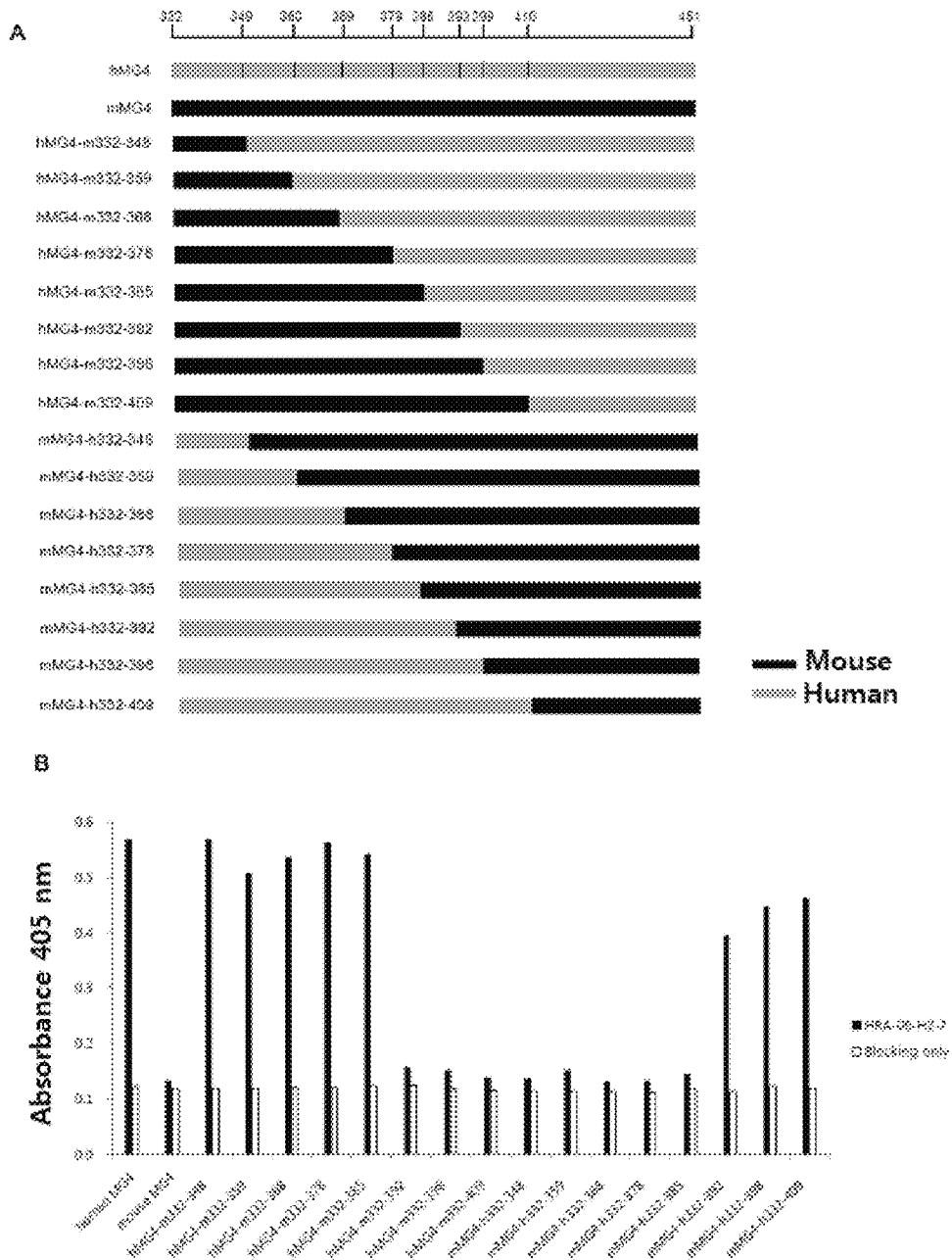
FIG. 14 shows that the antibody according to an exemplary embodiment of the present invention is bound to 386th to 392nd amino acid residues at N-terminus of the beta chain (55th to 61th amino acid sequences based on the MG4 domain sequence), as confirmed by ELISA.

Results thereof were shown in FIGS. 13 and 14.

FIG. 13A shows human/mouse hybrid MG4 domains, and FIG. 13B shows ELISA results. As shown in FIG. 13, the HRA-06-H2-7 antibody was bound when 379th to 398th amino acid residue sequences based on the beta chain sequence were human sequences, which shows binding possibility to the corresponding site of the antibody.

FIG. 14 shows results obtained by more specifically confirming the binding sites of the sequences. FIG. 14A shows human/mouse hybrid MG4 domains, and FIG. 14B shows ELISA results. As shown in FIG. 14, the HRA-06-H2-7 antibody was bound when 386th to 392nd amino acid residue sequences based on the beta chain sequence (55th to 61th amino acid sequences based on the MG4 domain sequence) were human sequences, which shows binding possibility to the corresponding site of the antibody.

What is claimed is:

1. A monoclonal antibody binding to human complement component 5 (C5) protein or antigen-binding fragment thereof, comprising a heavy chain CDR1 of SEQ ID NO: 1, a heavy chain CDR2 of SEQ ID NO: 2, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

2. A monoclonal antibody binding to human C5 protein or antigen-binding fragment thereof, comprising a heavy chain CDR1 of SEQ ID NO: 11, a heavy chain CDR2 of SEQ ID NO: 12, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

3. A monoclonal antibody binding to human C5 protein or antigen-binding fragment thereof, comprising a heavy chain CDR1 of SEQ ID NO: 21, a heavy chain CDR2 of SEQ ID NO: 22, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

4. A monoclonal antibody binding to human C5 protein or antigen-binding fragment thereof, comprising a heavy chain CDR1 of SEQ ID NO: 31, a heavy chain CDR2 of SEQ ID NO: 32, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

5. A monoclonal antibody binding to human C5 protein or antigen-binding fragment thereof, comprising a heavy chain CDR1 of SEQ ID NO: 41, a heavy chain CDR2 of SEQ ID NO: 42, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

6. A monoclonal antibody binding to human C5 protein or antigen-binding fragment thereof, comprising a heavy chain CDR1 of SEQ ID NO: 51, a heavy chain CDR2 of SEQ ID NO: 52, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6.

7. A monoclonal antibody binding to human C5 protein or antigen-binding fragment thereof, comprising a heavy chain variable region selected from the group consisting of SEQ ID NO: 7, 17, 27, 37, 47 and 57; and a light chain variable region of SEQ ID NO: 8.

8. A monoclonal antibody binding to human C5 protein or antigen-binding fragment thereof, comprising a heavy chain selected from the group consisting of SEQ ID NO: 9, 19, 29, 39, 49 and 59; and a light chain of SEQ ID NO: 10.

9. A pharmaceutical composition, comprising:

the antibody, the monoclonal antibody or antigen-binding fragment thereof according to any one of claims 1-6, 7, and 8.

10. A method for treating complement-related diseases, comprising:

administering a therapeutically effective amount of the antibody or antigen-binding fragment thereof of any one of claims 1-6, 7, and 8 to a subject in need thereof.

11. The method of claim 10, wherein the subject is a human.

12. The method of claim 11, wherein the complement-related diseases are selected from the group consisting of rheumatoid arthritis (RA), osteoarthritis, acute respiratory distress syndrome (ARDS), remote tissue injury after ischemia and reperfusion, complement activation during cardiopulmonary bypass surgery, dermatomyositis, pemphigus, lupus nephritis, glomerulonephritis, renal vasculitis, cardiopulmonary by-pass, heart failure-induced coronary endothelial dysfunction, type II membrane-proliferative glomerulonephritis, acute renal failure, antiphospholipid syndrome, macular degeneration, endophthalmitis, new blood vessel disease, allograft transplantation, hyperacute rejection, hemodialysis, chronic obstructive pulmonary disorder (COPD) respiratory distress syndrome, asthma, paroxysmal nocturnal hemoglobinuria (PNH) and aspiration pneumonia.

13. A kit for detecting a complement cleavage product in a subject with complement-related diseases, the kit comprising:

the antibody or antigen-binding fragment thereof according to any one of claims 1-6, 7, and 8; and
a container.

* * * * *

SEQUENCE LISTING

```
<160> NUMBER OF SEQ ID NOS: 145

<210> SEQ ID NO 1
<211> LENGTH: 11
<212> TYPE: PRT
<213> ORGANISM: Homo sapiens

<400> SEQUENCE: 1

Gly Phe Ser Phe Ser Gly Arg Tyr Trp Ile Gln
 1               5                  10

<210> SEQ ID NO 2
<211> LENGTH: 18
<212> TYPE: PRT
<213> ORGANISM: Homo sapiens

<400> SEQUENCE: 2

Ser Val Trp Pro Gly Ile Thr Gly Asp Thr Asn Tyr Ala Asn Trp Ala
 1               5                  10                  15

Lys Gly
```

<210> SEQ ID NO 3
<211> LENGTH: 11
<212> TYPE: PRT
<213> ORGANISM: Homo sapiens

<400> SEQUENCE: 3

Glu Pro Val Ala Trp Gly Gly Gly Leu Asp Leu
1               5                   10

<210> SEQ ID NO 4
<211> LENGTH: 11
<212> TYPE: PRT
<213> ORGANISM: Homo sapiens

<400> SEQUENCE: 4

Gln Ala Ser Gln Ser Ile Asn Asn Gln Leu Ser
1               5                   10

<210> SEQ ID NO 5
<211> LENGTH: 7
<212> TYPE: PRT
<213> ORGANISM: Homo sapiens

<400> SEQUENCE: 5

Tyr Ala Ser Thr Leu Ala Ser
1               5

<210> SEQ ID NO 6
<211> LENGTH: 12
<212> TYPE: PRT
<213> ORGANISM: Homo sapiens

<400> SEQUENCE: 6

Gln Gly Ser Tyr Tyr Ser Gly Gly Trp Asp Tyr Gly
1               5                   10

<210> SEQ ID NO 7
<211> LENGTH: 122
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
                20                  25                  30

Tyr Trp Ile Gln Trp Val Arg Gln Ala Pro Gly Lys Gly Leu Glu Trp
            35                  40                  45

Val Ala Ser Val Trp Pro Gly Ile Thr Gly Asp Thr Asn Tyr Ala Asn
        50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser
        115                 120

<210> SEQ ID NO 8

-continued

```
<211> LENGTH: 110
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Ser Gly Gly
                85                  90                  95

Trp Asp Tyr Gly Phe Gly Gln Gly Thr Lys Val Glu Ile Lys
                100                 105                 110

<210> SEQ ID NO 9
<211> LENGTH: 448
<212> TYPE: PRT
<213> ORGANISM: Homo sapiens

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Val Trp Pro Gly Ile Thr Gly Asp Thr Asn Tyr Ala Asn
    50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 10
<211> LENGTH: 217
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                165                 170                 175
Ser Leu Ser Ser Thr Leu Thr Leu Ser Lys Ala Asp Tyr Glu Lys His
        180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
        210                 215

<210> SEQ ID NO 11
<211> LENGTH: 11
<212> TYPE: PRT
<213> ORGANISM: Homo sapiens

<400> SEQUENCE: 11

Gly Phe Ser Phe Ser Gly Arg Tyr Trp Ile Gln
1               5                   10

<210> SEQ ID NO 12
<211> LENGTH: 18
<212> TYPE: PRT
<213> ORGANISM: Homo sapiens

<400> SEQUENCE: 12

Ser Gly Trp Pro Gly Ala Thr Gly Asp Thr Asn Tyr Ala Asn Trp Ala
1               5                   10                  15

Lys Gly

<210> SEQ ID NO 13
<211> LENGTH: 11
<212> TYPE: PRT
<213> ORGANISM: Homo sapiens

<400> SEQUENCE: 13

Glu Pro Val Ala Trp Gly Gly Gly Leu Asp Leu
1               5                   10

<210> SEQ ID NO 14
<211> LENGTH: 11
<212> TYPE: PRT
<213> ORGANISM: Homo sapiens

<400> SEQUENCE: 14

Gln Ala Ser Gln Ser Ile Asn Asn Gln Leu Ser
1               5                   10

<210> SEQ ID NO 15
<211> LENGTH: 7
<212> TYPE: PRT
<213> ORGANISM: Homo sapiens

<400> SEQUENCE: 15

Tyr Ala Ser Thr Leu Ala Ser
1               5

<210> SEQ ID NO 16
<211> LENGTH: 12
<212> TYPE: PRT
<213> ORGANISM: Homo sapiens

<400> SEQUENCE: 16

Gln Gly Ser Tyr Tyr Ser Gly Gly Trp Asp Tyr Gly
1               5                   10
```

<210> SEQ ID NO 17
<211> LENGTH: 122
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Gly Trp Pro Gly Ala Thr Gly Asp Thr Asn Tyr Ala Asn
    50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Leu Asp Leu Trp
            100                 105                 110

Gly Gln Gly Thr Leu Val Thr Val Ser Ser
        115                 120

<210> SEQ ID NO 18
<211> LENGTH: 110
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys
            100                 105                 110

<210> SEQ ID NO 19
<211> LENGTH: 448
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Gly Trp Pro Gly Ala Thr Gly Asp Thr Asn Tyr Ala Asn 50                  55                  60
Trp Ala Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                     85                  90                  95

Tyr Cys Ala Arg Glu Pro Val Ala Trp Gly Gly Leu Asp Leu Trp
                100                 105                 110

Gly Gln Gly Thr Leu Val Thr Val Ser Ala Ser Thr Lys Gly Pro
                115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
                195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
                260                 265                 270

Glu Val Gln Phe Asn Trp Tyr Val Asp Gly Val Glu Val His Asn Ala
                275                 280                 285

Lys Thr Lys Pro Arg Glu Glu Gln Phe Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 20
<211> LENGTH: 217
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
210                 215

<210> SEQ ID NO 21
<211> LENGTH: 11
<212> TYPE: PRT
<213> ORGANISM: Homo sapiens

<400> SEQUENCE: 21

Gly Phe Ser Phe Ser Gly Arg Tyr Trp Ile Gln
1               5                   10

<210> SEQ ID NO 22
<211> LENGTH: 18
<212> TYPE: PRT
<213> ORGANISM: Homo sapiens

<400> SEQUENCE: 22

Ser Ser Ser Leu Arg Gly Thr Gly Asp Thr Asn Tyr Ala Asn Trp Ala
1               5                   10                  15

Lys Gly

<210> SEQ ID NO 23
<211> LENGTH: 11
<212> TYPE: PRT
<213> ORGANISM: Homo sapiens

<400> SEQUENCE: 23

Glu Pro Val Ala Trp Gly Gly Gly Leu Asp Leu
1               5                   10

<210> SEQ ID NO 24
<211> LENGTH: 11
<212> TYPE: PRT
<213> ORGANISM: Homo sapiens

<400> SEQUENCE: 24

Gln Ala Ser Gln Ser Ile Asn Asn Gln Leu Ser
1               5                   10

<210> SEQ ID NO 25
<211> LENGTH: 7
<212> TYPE: PRT
<213> ORGANISM: Homo sapiens

<400> SEQUENCE: 25

Tyr Ala Ser Thr Leu Ala Ser
1               5

<210> SEQ ID NO 26
<211> LENGTH: 12
<212> TYPE: PRT
<213> ORGANISM: Homo sapiens

<400> SEQUENCE: 26

Gln Gly Ser Tyr Tyr Ser Gly Gly Trp Asp Tyr Gly
1               5                   10

<210> SEQ ID NO 27
<211> LENGTH: 122
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Ser Ser Leu Arg Gly Thr Gly Asp Thr Asn Tyr Ala Asn
    50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser
        115                 120

<210> SEQ ID NO 28
<211> LENGTH: 110
<212> TYPE: PRT
<213> ORGANISM: Homo sapiens

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

```
Leu Ser Trp Tyr Gln Gln Lys Pro Gly Lys Ala Pro Lys Leu Leu Ile
             35                  40                  45

Tyr Tyr Ala Ser Thr Leu Ala Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Ser Tyr Tyr Ser Gly Gly
                 85                  90                  95

Trp Asp Tyr Gly Phe Gly Gln Gly Thr Lys Val Glu Ile Lys
            100                 105                 110

<210> SEQ ID NO 29
<211> LENGTH: 448
<212> TYPE: PRT
<213> ORGANISM: Homo sapiens

<400> SEQUENCE: 29

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Phe Ser Gly Arg
             20                  25                  30

Tyr Trp Ile Gln Trp Val Arg Gln Ala Pro Gly Lys Gly Leu Glu Trp
         35                  40                  45

Val Ala Ser Ser Leu Arg Gly Thr Gly Asp Thr Asn Tyr Ala Asn
     50                  55                  60

Trp Ala Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Pro Val Ala Trp Gly Gly Leu Asp Leu Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
```

```
            290                 295                 300
Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 30
<211> LENGTH: 217
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 31
<211> LENGTH: 11
<212> TYPE: PRT
<213> ORGANISM: Homo sapiens

<400> SEQUENCE: 31

Gly Phe Ser Phe Ser Gly Arg Tyr Trp Ile Gln
 1               5                  10

<210> SEQ ID NO 32
<211> LENGTH: 18
<212> TYPE: PRT
<213> ORGANISM: Homo sapiens

<400> SEQUENCE: 32

Ser Val Trp Pro Gly Phe Thr Gly Asp Thr Asn Tyr Ala Asn Trp Ala
 1               5                  10                  15

Lys Gly

<210> SEQ ID NO 33
<211> LENGTH: 11
<212> TYPE: PRT
<213> ORGANISM: Homo sapiens

<400> SEQUENCE: 33

Glu Pro Val Ala Trp Gly Gly Gly Leu Asp Leu
 1               5                  10

<210> SEQ ID NO 34
<211> LENGTH: 11
<212> TYPE: PRT
<213> ORGANISM: Homo sapiens

<400> SEQUENCE: 34

Gln Ala Ser Gln Ser Ile Asn Asn Gln Leu Ser
 1               5                  10

<210> SEQ ID NO 35
<211> LENGTH: 7
<212> TYPE: PRT
<213> ORGANISM: Homo sapiens

<400> SEQUENCE: 35

Tyr Ala Ser Thr Leu Ala Ser
 1               5

<210> SEQ ID NO 36
<211> LENGTH: 12
<212> TYPE: PRT
<213> ORGANISM: Homo sapiens

<400> SEQUENCE: 36

Gln Gly Ser Tyr Tyr Ser Gly Gly Trp Asp Tyr Gly
 1               5                  10

<210> SEQ ID NO 37
<211> LENGTH: 122
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
 1               5                  10                  15

```
Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Val Trp Pro Gly Phe Thr Gly Asp Thr Asn Tyr Ala Asn
    50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser
            115                 120

<210> SEQ ID NO 38
<211> LENGTH: 110
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys
            100                 105                 110

<210> SEQ ID NO 39
<211> LENGTH: 448
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Gly Arg
            20                  25                  30

Tyr Trp Ile Gln Trp Val Arg Gln Ala Pro Gly Lys Gly Leu Glu Trp
        35                  40                  45

Val Ala Ser Val Trp Pro Gly Phe Thr Gly Asp Thr Asn Tyr Ala Asn
    50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110
```

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 40
<211> LENGTH: 217
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Ser Tyr Tyr Ser Gly Gly
                 85                  90                  95

Trp Asp Tyr Gly Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 41
<211> LENGTH: 11
<212> TYPE: PRT
<213> ORGANISM: Homo sapiens

<400> SEQUENCE: 41

Gly Phe Ser Leu Ser Gly Arg Tyr Trp Ile Gln
 1               5                  10

<210> SEQ ID NO 42
<211> LENGTH: 18
<212> TYPE: PRT
<213> ORGANISM: Homo sapiens

<400> SEQUENCE: 42

Ser Gly Trp Pro Gly Ala Thr Gly Asp Thr Asn Tyr Ala Asn Trp Ala
 1               5                  10                  15

Lys Gly

<210> SEQ ID NO 43
<211> LENGTH: 11
<212> TYPE: PRT
<213> ORGANISM: Homo sapiens

<400> SEQUENCE: 43

Glu Pro Val Ala Trp Gly Gly Gly Leu Asp Leu
 1               5                  10

<210> SEQ ID NO 44
<211> LENGTH: 11
<212> TYPE: PRT
<213> ORGANISM: Homo sapiens

<400> SEQUENCE: 44

Gln Ala Ser Gln Ser Ile Asn Asn Gln Leu Ser
 1               5                  10

<210> SEQ ID NO 45
<211> LENGTH: 7
<212> TYPE: PRT
<213> ORGANISM: Homo sapiens

<400> SEQUENCE: 45

Tyr Ala Ser Thr Leu Ala Ser
 1               5

<210> SEQ ID NO 46
<211> LENGTH: 12
<212> TYPE: PRT
<213> ORGANISM: Homo sapiens

<400> SEQUENCE: 46

Gln Gly Ser Tyr Tyr Ser Gly Gly Trp Asp Tyr Gly
 1               5                  10

<210> SEQ ID NO 47
<211> LENGTH: 122
<212> TYPE: PRT
<213> ORGANISM: Homo sapiens

<400> SEQUENCE: 47

Glu Val Gln Leu Val Glu Ser Gly Gly Leu Val Gln Pro Gly Gly
 1               5                  10                  15

Ser Leu Arg Leu Ser Cys Ala Ala Ser Gly Phe Ser Leu Ser Gly Arg
             20                  25                  30

Tyr Trp Ile Gln Trp Val Arg Gln Ala Pro Gly Lys Gly Leu Glu Trp
         35                  40                  45

Val Ala Ser Gly Trp Pro Gly Ala Thr Gly Asp Thr Asn Tyr Ala Asn
     50                  55                  60

Trp Ala Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser
        115                 120

<210> SEQ ID NO 48
<211> LENGTH: 110
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Asn Asn Gln
             20                  25                  30

Leu Ser Trp Tyr Gln Gln Lys Pro Gly Lys Ala Pro Lys Leu Leu Ile
         35                  40                  45

Tyr Tyr Ala Ser Thr Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gly Ser Tyr Tyr Ser Gly Gly

```
                    85                  90                  95
Trp Asp Tyr Gly Phe Gly Gln Gly Thr Lys Val Glu Ile Lys
                100                 105                 110

<210> SEQ ID NO 49
<211> LENGTH: 448
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ser Leu Ser Gly Arg
                 20                  25                  30

Tyr Trp Ile Gln Trp Val Arg Gln Ala Pro Gly Lys Gly Leu Glu Trp
             35                  40                  45

Val Ala Ser Gly Trp Pro Gly Ala Thr Gly Asp Thr Asn Tyr Ala Asn
         50                  55                  60

Trp Ala Lys Gly Arg Phe Thr Ile Ser Arg Asp Asp Ser Lys Asn Thr
 65                  70                  75                  80

Leu Tyr Leu Gln Met Asn Ser Leu Arg Ala Glu Asp Thr Ala Val Tyr
                 85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350
```

```
Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445
```

<210> SEQ ID NO 50
<211> LENGTH: 217
<212> TYPE: PRT
<213> ORGANISM: Homo sapiens

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
                180                 185                 190

Lys Val Tyr Ala Cys Glu Val Thr His Gln Gly Leu Ser Ser Pro Val
            195                 200                 205

Thr Lys Ser Phe Asn Arg Gly Glu Cys
    210                 215
```

<210> SEQ ID NO 51
<211> LENGTH: 11
<212> TYPE: PRT
<213> ORGANISM: Homo sapiens

<400> SEQUENCE: 51

```
Gly Phe Ser Leu Ser Gly Arg Tyr Trp Ile Gln
1               5                   10
```

<210> SEQ ID NO 52
<211> LENGTH: 18
<212> TYPE: PRT
<213> ORGANISM: Homo sapiens

<400> SEQUENCE: 52

Ser Val Trp Pro Gly Phe Thr Gly Asp Thr Asn Tyr Ala Asn Trp Ala
 1               5                   10                  15

Lys Gly

<210> SEQ ID NO 53
<211> LENGTH: 11
<212> TYPE: PRT
<213> ORGANISM: Homo sapiens

<400> SEQUENCE: 53

Glu Pro Val Ala Trp Gly Gly Gly Leu Asp Leu
 1               5                   10

<210> SEQ ID NO 54
<211> LENGTH: 11
<212> TYPE: PRT
<213> ORGANISM: Homo sapiens

<400> SEQUENCE: 54

Gln Ala Ser Gln Ser Ile Asn Asn Gln Leu Ser
 1               5                   10

<210> SEQ ID NO 55
<211> LENGTH: 7
<212> TYPE: PRT
<213> ORGANISM: Homo sapiens

<400> SEQUENCE: 55

Tyr Ala Ser Thr Leu Ala Ser
 1               5

<210> SEQ ID NO 56
<211> LENGTH: 12
<212> TYPE: PRT
<213> ORGANISM: Homo sapiens

<400> SEQUENCE: 56

Gln Gly Ser Tyr Tyr Ser Gly Gly Trp Asp Tyr Gly
 1               5                   10

<210> SEQ ID NO 57
<211> LENGTH: 122
<212> TYPE: PRT
<213> ORGANISM: Homo sapiens

<400> SEQUENCE: 57

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Ser Leu Ser Gly Arg
                20                  25                  30

Tyr Trp Ile Gln Trp Val Arg Gln Ala Pro Gly Lys Gly Leu Glu Trp
            35                  40                  45

Val Ala Ser Val Trp Pro Gly Phe Thr Gly Asp Thr Asn Tyr Ala Asn
        50                  55                  60

Trp Ala Lys Gly Arg Phe Thr Ile Ser Arg Asp Asp Ser Lys Asn Thr
65                  70                  75                  80

```
Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser
            115                 120

<210> SEQ ID NO 58
<211> LENGTH: 110
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys
            100                 105                 110

<210> SEQ ID NO 59
<211> LENGTH: 448
<212> TYPE: PRT
<213> ORGANISM: Homo sapiens

<400> SEQUENCE: 59

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Gly Arg
            20                  25                  30

Tyr Trp Ile Gln Trp Val Arg Gln Ala Pro Gly Lys Gly Leu Glu Trp
        35                  40                  45

Val Ala Ser Val Trp Pro Gly Phe Thr Gly Asp Thr Asn Tyr Ala Asn
 50                  55                  60

Trp Ala Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Pro Val Ala Trp Gly Gly Gly Leu Asp Leu Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 60
<211> LENGTH: 217
<212> TYPE: PRT
<213> ORGANISM: Homo sapiens

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Gln
            20                  25                  30

Leu Ser Trp Tyr Gln Gln Lys Pro Gly Lys Ala Pro Lys Leu Leu Ile
        35                  40                  45

Tyr Tyr Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ser Tyr Tyr Ser Gly Gly
                85                  90                  95

Trp Asp Tyr Gly Phe Gly Gln Gly Thr Lys Val Glu Ile Lys Arg Thr

```
                100                 105                 110
Val Ala Ala Pro Ser Val Phe Ile Phe Pro Ser Asp Glu Gln Leu
            115                 120                 125
Lys Ser Gly Thr Ala Ser Val Val Cys Leu Leu Asn Asn Phe Tyr Pro
130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
210                 215

<210> SEQ ID NO 61
<211> LENGTH: 1676
<212> TYPE: PRT
<213> ORGANISM: Homo sapiens

<400> SEQUENCE: 61

Met Gly Leu Leu Gly Ile Leu Cys Phe Leu Ile Phe Leu Gly Lys Thr
1               5                   10                  15
Trp Gly Gln Glu Gln Thr Tyr Val Ile Ser Ala Pro Lys Ile Phe Arg
                20                  25                  30
Val Gly Ala Ser Glu Asn Ile Val Ile Gln Val Tyr Gly Tyr Thr Glu
            35                  40                  45
Ala Phe Asp Ala Thr Ile Ser Ile Lys Ser Tyr Pro Asp Lys Lys Phe
        50                  55                  60
Ser Tyr Ser Ser Gly His Val His Leu Ser Ser Glu Asn Lys Phe Gln
65                  70                  75                  80
Asn Ser Ala Ile Leu Thr Ile Gln Pro Lys Gln Leu Pro Gly Gly Gln
                85                  90                  95
Asn Pro Val Ser Tyr Val Tyr Leu Glu Val Val Ser Lys His Phe Ser
            100                 105                 110
Lys Ser Lys Arg Met Pro Ile Thr Tyr Asp Asn Gly Phe Leu Phe Ile
        115                 120                 125
His Thr Asp Lys Pro Val Tyr Thr Pro Asp Gln Ser Val Lys Val Arg
130                 135                 140
Val Tyr Ser Leu Asn Asp Asp Leu Lys Pro Ala Lys Arg Glu Thr Val
145                 150                 155                 160
Leu Thr Phe Ile Asp Pro Glu Gly Ser Glu Val Asp Met Val Glu Glu
                165                 170                 175
Ile Asp His Ile Gly Ile Ile Ser Phe Pro Asp Phe Lys Ile Pro Ser
            180                 185                 190
Asn Pro Arg Tyr Gly Met Trp Thr Ile Lys Ala Lys Tyr Lys Glu Asp
        195                 200                 205
Phe Ser Thr Thr Gly Thr Ala Tyr Phe Glu Val Lys Glu Tyr Val Leu
210                 215                 220
Pro His Phe Ser Val Ser Ile Glu Pro Glu Tyr Asn Phe Ile Gly Tyr
225                 230                 235                 240
Lys Asn Phe Lys Asn Phe Glu Ile Thr Ile Lys Ala Arg Tyr Phe Tyr
                245                 250                 255
```

-continued

```
Asn Lys Val Val Thr Glu Ala Asp Val Tyr Ile Thr Phe Gly Ile Arg
            260                 265                 270
Glu Asp Leu Lys Asp Asp Gln Lys Glu Met Met Gln Thr Ala Met Gln
        275                 280                 285
Asn Thr Met Leu Ile Asn Gly Ile Ala Gln Val Thr Phe Asp Ser Glu
    290                 295                 300
Thr Ala Val Lys Glu Leu Ser Tyr Tyr Ser Leu Glu Asp Leu Asn Asn
305                 310                 315                 320
Lys Tyr Leu Tyr Ile Ala Val Thr Val Ile Glu Ser Thr Gly Gly Phe
                325                 330                 335
Ser Glu Glu Ala Glu Ile Pro Gly Ile Lys Tyr Val Leu Ser Pro Tyr
            340                 345                 350
Lys Leu Asn Leu Val Ala Thr Pro Leu Phe Leu Lys Pro Gly Ile Pro
        355                 360                 365
Tyr Pro Ile Lys Val Gln Val Lys Asp Ser Leu Asp Gln Leu Val Gly
    370                 375                 380
Gly Val Pro Val Thr Leu Asn Ala Gln Thr Ile Asp Val Asn Gln Glu
385                 390                 395                 400
Thr Ser Asp Leu Asp Pro Ser Lys Ser Val Thr Arg Val Asp Asp Gly
                405                 410                 415
Val Ala Ser Phe Val Leu Asn Leu Pro Ser Gly Val Thr Val Leu Glu
            420                 425                 430
Phe Asn Val Lys Thr Asp Ala Pro Asp Leu Pro Glu Glu Asn Gln Ala
        435                 440                 445
Arg Glu Gly Tyr Arg Ala Ile Ala Tyr Ser Ser Leu Ser Gln Ser Tyr
    450                 455                 460
Leu Tyr Ile Asp Trp Thr Asp Asn His Lys Ala Leu Leu Val Gly Glu
465                 470                 475                 480
His Leu Asn Ile Ile Val Thr Pro Lys Ser Pro Tyr Ile Asp Lys Ile
                485                 490                 495
Thr His Tyr Asn Tyr Leu Ile Leu Ser Lys Gly Lys Ile Ile His Phe
            500                 505                 510
Gly Thr Arg Glu Lys Phe Ser Asp Ala Ser Tyr Gln Ser Ile Asn Ile
        515                 520                 525
Pro Val Thr Gln Asn Met Val Pro Ser Ser Arg Leu Leu Val Tyr Tyr
    530                 535                 540
Ile Val Thr Gly Glu Gln Thr Ala Glu Leu Val Ser Asp Ser Val Trp
545                 550                 555                 560
Leu Asn Ile Glu Glu Lys Cys Gly Asn Gln Leu Gln Val His Leu Ser
                565                 570                 575
Pro Asp Ala Asp Ala Tyr Ser Pro Gly Gln Thr Val Ser Leu Asn Met
            580                 585                 590
Ala Thr Gly Met Asp Ser Trp Val Ala Leu Ala Val Asp Ser Ala
        595                 600                 605
Val Tyr Gly Val Gln Arg Gly Ala Lys Lys Pro Leu Glu Arg Val Phe
    610                 615                 620
Gln Phe Leu Glu Lys Ser Asp Leu Gly Cys Gly Ala Gly Gly Gly Leu
625                 630                 635                 640
Asn Asn Ala Asn Val Phe His Leu Ala Gly Leu Thr Phe Leu Thr Asn
                645                 650                 655
Ala Asn Ala Asp Asp Ser Gln Glu Asn Asp Glu Pro Cys Lys Glu Ile
            660                 665                 670
Leu Arg Pro Arg Arg Thr Leu Gln Lys Lys Ile Glu Glu Ile Ala Ala
```

```
                675                 680                 685
Lys Tyr Lys His Ser Val Val Lys Cys Cys Tyr Asp Gly Ala Cys
690                 695                 700
Val Asn Asn Asp Glu Thr Cys Glu Gln Arg Ala Ala Arg Ile Ser Leu
705                 710                 715                 720
Gly Pro Arg Cys Ile Lys Ala Phe Thr Glu Cys Cys Val Val Ala Ser
                725                 730                 735
Gln Leu Arg Ala Asn Ile Ser His Lys Asp Met Gln Leu Gly Arg Leu
            740                 745                 750
His Met Lys Thr Leu Leu Pro Val Ser Lys Pro Glu Ile Arg Ser Tyr
        755                 760                 765
Phe Pro Glu Ser Trp Leu Trp Glu Val His Leu Val Pro Arg Arg Lys
    770                 775                 780
Gln Leu Gln Phe Ala Leu Pro Asp Ser Leu Thr Thr Trp Glu Ile Gln
785                 790                 795                 800
Gly Val Gly Ile Ser Asn Thr Gly Ile Cys Val Ala Asp Thr Val Lys
                805                 810                 815
Ala Lys Val Phe Lys Asp Val Phe Leu Glu Met Asn Ile Pro Tyr Ser
            820                 825                 830
Val Val Arg Gly Glu Gln Ile Gln Leu Lys Gly Thr Val Tyr Asn Tyr
        835                 840                 845
Arg Thr Ser Gly Met Gln Phe Cys Val Lys Met Ser Ala Val Glu Gly
    850                 855                 860
Ile Cys Thr Ser Glu Ser Pro Val Ile Asp His Gln Gly Thr Lys Ser
865                 870                 875                 880
Ser Lys Cys Val Arg Gln Lys Val Glu Gly Ser Ser Ser His Leu Val
                885                 890                 895
Thr Phe Thr Val Leu Pro Leu Glu Ile Gly Leu His Asn Ile Asn Phe
            900                 905                 910
Ser Leu Glu Thr Trp Phe Gly Lys Glu Ile Leu Val Lys Thr Leu Arg
        915                 920                 925
Val Val Pro Glu Gly Val Lys Arg Glu Ser Tyr Ser Gly Val Thr Leu
    930                 935                 940
Asp Pro Arg Gly Ile Tyr Gly Thr Ile Ser Arg Arg Lys Glu Phe Pro
945                 950                 955                 960
Tyr Arg Ile Pro Leu Asp Leu Val Pro Lys Thr Glu Ile Lys Arg Ile
                965                 970                 975
Leu Ser Val Lys Gly Leu Leu Val Gly Glu Ile Leu Ser Ala Val Leu
            980                 985                 990
Ser Gln Glu Gly Ile Asn Ile Leu Thr His Leu Pro Lys Gly Ser Ala
        995                 1000                1005
Glu Ala Glu Leu Met Ser Val Val Pro Val Phe Tyr Val Phe His Tyr
    1010                1015                1020
Leu Glu Thr Gly Asn His Trp Asn Ile Phe His Ser Asp Pro Leu Ile
1025                1030                1035                1040
Glu Lys Gln Lys Leu Lys Lys Lys Leu Lys Glu Gly Met Leu Ser Ile
                1045                1050                1055
Met Ser Tyr Arg Asn Ala Asp Tyr Ser Tyr Ser Val Trp Lys Gly Gly
            1060                1065                1070
Ser Ala Ser Thr Trp Leu Thr Ala Phe Ala Leu Arg Val Leu Gly Gln
        1075                1080                1085
Val Asn Lys Tyr Val Glu Gln Asn Gln Asn Ser Ile Cys Asn Ser Leu
    1090                1095                1100
```

```
Leu Trp Leu Val Glu Asn Tyr Gln Leu Asp Asn Gly Ser Phe Lys Glu
1105                1110                1115                1120

Asn Ser Gln Tyr Gln Pro Ile Lys Leu Gln Gly Thr Leu Pro Val Glu
            1125                1130                1135

Ala Arg Glu Asn Ser Leu Tyr Leu Thr Ala Phe Thr Val Ile Gly Ile
        1140                1145                1150

Arg Lys Ala Phe Asp Ile Cys Pro Leu Val Lys Ile Asp Thr Ala Leu
    1155                1160                1165

Ile Lys Ala Asp Asn Phe Leu Leu Glu Asn Thr Leu Pro Ala Gln Ser
1170                1175                1180

Thr Phe Thr Leu Ala Ile Ser Ala Tyr Ala Leu Ser Leu Gly Asp Lys
1185                1190                1195                1200

Thr His Pro Gln Phe Arg Ser Ile Val Ser Ala Leu Lys Arg Glu Ala
                1205                1210                1215

Leu Val Lys Gly Asn Pro Pro Ile Tyr Arg Phe Trp Lys Asp Asn Leu
            1220                1225                1230

Gln His Lys Asp Ser Ser Val Pro Asn Thr Gly Thr Ala Arg Met Val
        1235                1240                1245

Glu Thr Thr Ala Tyr Ala Leu Leu Thr Ser Leu Asn Leu Lys Asp Ile
    1250                1255                1260

Asn Tyr Val Asn Pro Val Ile Lys Trp Leu Ser Glu Glu Gln Arg Tyr
1265                1270                1275                1280

Gly Gly Gly Phe Tyr Ser Thr Gln Asp Thr Ile Asn Ala Ile Glu Gly
                1285                1290                1295

Leu Thr Glu Tyr Ser Leu Leu Val Lys Gln Leu Arg Leu Ser Met Asp
            1300                1305                1310

Ile Asp Val Ser Tyr Lys His Lys Gly Ala Leu His Asn Tyr Lys Met
        1315                1320                1325

Thr Asp Lys Asn Phe Leu Gly Arg Pro Val Glu Val Leu Leu Asn Asp
    1330                1335                1340

Asp Leu Ile Val Ser Thr Gly Phe Gly Ser Gly Leu Ala Thr Val His
1345                1350                1355                1360

Val Thr Thr Val Val His Lys Thr Ser Thr Ser Glu Glu Val Cys Ser
                1365                1370                1375

Phe Tyr Leu Lys Ile Asp Thr Gln Asp Ile Glu Ala Ser His Tyr Arg
            1380                1385                1390

Gly Tyr Gly Asn Ser Asp Tyr Lys Arg Ile Val Ala Cys Ala Ser Tyr
        1395                1400                1405

Lys Pro Ser Arg Glu Glu Ser Ser Gly Ser Ser His Ala Val Met
    1410                1415                1420

Asp Ile Ser Leu Pro Thr Gly Ile Ser Ala Asn Glu Glu Asp Leu Lys
1425                1430                1435                1440

Ala Leu Val Glu Gly Val Asp Gln Leu Phe Thr Asp Tyr Gln Ile Lys
                1445                1450                1455

Asp Gly His Val Ile Leu Gln Leu Asn Ser Ile Pro Ser Ser Asp Phe
            1460                1465                1470

Leu Cys Val Arg Phe Arg Ile Phe Glu Leu Phe Glu Val Gly Phe Leu
        1475                1480                1485

Ser Pro Ala Thr Phe Thr Val Tyr Glu Tyr His Arg Pro Asp Lys Gln
    1490                1495                1500

Cys Thr Met Phe Tyr Ser Thr Ser Asn Ile Lys Ile Gln Lys Val Cys
1505                1510                1515                1520
```

```
Glu Gly Ala Ala Cys Lys Cys Val Glu Ala Asp Cys Gly Gln Met Gln
            1525                1530                1535

Glu Glu Leu Asp Leu Thr Ile Ser Ala Glu Thr Arg Lys Gln Thr Ala
            1540                1545                1550

Cys Lys Pro Glu Ile Ala Tyr Ala Tyr Lys Val Ser Ile Thr Ser Ile
            1555                1560                1565

Thr Val Glu Asn Val Phe Val Lys Tyr Lys Ala Thr Leu Leu Asp Ile
        1570                1575                1580

Tyr Lys Thr Gly Glu Ala Val Ala Glu Lys Asp Ser Glu Ile Thr Phe
1585                1590                1595                1600

Ile Lys Lys Val Thr Cys Thr Asn Ala Glu Leu Val Lys Gly Arg Gln
            1605                1610                1615

Tyr Leu Ile Met Gly Lys Glu Ala Leu Gln Ile Lys Tyr Asn Phe Ser
            1620                1625                1630

Phe Arg Tyr Ile Tyr Pro Leu Asp Ser Leu Thr Trp Ile Glu Tyr Trp
            1635                1640                1645

Pro Arg Asp Thr Thr Cys Ser Ser Cys Gln Ala Phe Leu Ala Asn Leu
            1650                1655                1660

Asp Glu Phe Ala Glu Asp Ile Phe Leu Asn Gly Cys
1665                1670                1675

<210> SEQ ID NO 62
<211> LENGTH: 673
<212> TYPE: PRT
<213> ORGANISM: Homo sapiens

<400> SEQUENCE: 62

Met Gly Leu Leu Gly Ile Leu Cys Phe Leu Ile Phe Leu Gly Lys Thr
1               5                   10                  15

Trp Gly Gln Glu Gln Thr Tyr Val Ile Ser Ala Pro Lys Ile Phe Arg
            20                  25                  30

Val Gly Ala Ser Glu Asn Ile Val Ile Gln Val Tyr Gly Tyr Thr Glu
        35                  40                  45

Ala Phe Asp Ala Thr Ile Ser Ile Lys Ser Tyr Pro Asp Lys Lys Phe
    50                  55                  60

Ser Tyr Ser Ser Gly His Val His Leu Ser Ser Glu Asn Lys Phe Gln
65                  70                  75                  80

Asn Ser Ala Ile Leu Thr Ile Gln Pro Lys Gln Leu Pro Gly Gly Gln
                85                  90                  95

Asn Pro Val Ser Tyr Val Tyr Leu Glu Val Val Ser Lys His Phe Ser
            100                 105                 110

Lys Ser Lys Arg Met Pro Ile Thr Tyr Asp Asn Gly Phe Leu Phe Ile
            115                 120                 125

His Thr Asp Lys Pro Val Tyr Thr Pro Asp Gln Ser Val Lys Val Arg
        130                 135                 140

Val Tyr Ser Leu Asn Asp Asp Leu Lys Pro Ala Lys Arg Glu Thr Val
145                 150                 155                 160

Leu Thr Phe Ile Asp Pro Glu Gly Ser Glu Val Asp Met Val Glu Glu
                165                 170                 175

Ile Asp His Ile Gly Ile Ile Ser Phe Pro Asp Phe Lys Ile Pro Ser
            180                 185                 190

Asn Pro Arg Tyr Gly Met Trp Thr Ile Lys Ala Lys Tyr Lys Glu Asp
            195                 200                 205

Phe Ser Thr Thr Gly Thr Ala Tyr Phe Glu Val Lys Glu Tyr Val Leu
        210                 215                 220
```

-continued

Pro His Phe Ser Val Ser Ile Glu Pro Glu Tyr Asn Phe Ile Gly Tyr
225                 230                 235                 240

Lys Asn Phe Lys Asn Phe Glu Ile Thr Ile Lys Ala Arg Tyr Phe Tyr
            245                 250                 255

Asn Lys Val Val Thr Glu Ala Asp Val Tyr Ile Thr Phe Gly Ile Arg
                260                 265                 270

Glu Asp Leu Lys Asp Asp Gln Lys Glu Met Met Gln Thr Ala Met Gln
            275                 280                 285

Asn Thr Met Leu Ile Asn Gly Ile Ala Gln Val Thr Phe Asp Ser Glu
            290                 295                 300

Thr Ala Val Lys Glu Leu Ser Tyr Tyr Ser Leu Glu Asp Leu Asn Asn
305                 310                 315                 320

Lys Tyr Leu Tyr Ile Ala Val Thr Val Ile Glu Ser Thr Gly Gly Phe
                325                 330                 335

Ser Glu Glu Ala Glu Ile Pro Gly Ile Lys Tyr Val Leu Ser Pro Tyr
            340                 345                 350

Lys Leu Asn Leu Val Ala Thr Pro Leu Phe Leu Lys Pro Gly Ile Pro
            355                 360                 365

Tyr Pro Ile Lys Val Gln Val Lys Asp Ser Leu Asp Gln Leu Val Gly
    370                 375                 380

Gly Val Pro Val Thr Leu Asn Ala Gln Thr Ile Asp Val Asn Gln Glu
385                 390                 395                 400

Thr Ser Asp Leu Asp Pro Ser Lys Ser Val Thr Arg Val Asp Asp Gly
            405                 410                 415

Val Ala Ser Phe Val Leu Asn Leu Pro Ser Gly Val Thr Val Leu Glu
            420                 425                 430

Phe Asn Val Lys Thr Asp Ala Pro Asp Leu Pro Glu Glu Asn Gln Ala
            435                 440                 445

Arg Glu Gly Tyr Arg Ala Ile Ala Tyr Ser Ser Leu Ser Gln Ser Tyr
    450                 455                 460

Leu Tyr Ile Asp Trp Thr Asp Asn His Lys Ala Leu Leu Val Gly Glu
465                 470                 475                 480

His Leu Asn Ile Ile Val Thr Pro Lys Ser Pro Tyr Ile Asp Lys Ile
                485                 490                 495

Thr His Tyr Asn Tyr Leu Ile Leu Ser Lys Gly Lys Ile Ile His Phe
            500                 505                 510

Gly Thr Arg Glu Lys Phe Ser Asp Ala Ser Tyr Gln Ser Ile Asn Ile
            515                 520                 525

Pro Val Thr Gln Asn Met Val Pro Ser Ser Arg Leu Leu Val Tyr Tyr
    530                 535                 540

Ile Val Thr Gly Glu Gln Thr Ala Glu Leu Val Ser Asp Ser Val Trp
545                 550                 555                 560

Leu Asn Ile Glu Glu Lys Cys Gly Asn Gln Leu Gln Val His Leu Ser
            565                 570                 575

Pro Asp Ala Asp Ala Tyr Ser Pro Gly Gln Thr Val Ser Leu Asn Met
    580                 585                 590

Ala Thr Gly Met Asp Ser Trp Val Ala Leu Ala Ala Val Asp Ser Ala
        595                 600                 605

Val Tyr Gly Val Gln Arg Gly Ala Lys Lys Pro Leu Glu Arg Val Phe
    610                 615                 620

Gln Phe Leu Glu Lys Ser Asp Leu Gly Cys Gly Ala Gly Gly Gly Leu
625                 630                 635                 640

```
Asn Asn Ala Asn Val Phe His Leu Ala Gly Leu Thr Phe Leu Thr Asn
            645                 650                 655

Ala Asn Ala Asp Asp Ser Gln Glu Asn Asp Glu Pro Cys Lys Glu Ile
        660                 665                 670

Leu

<210> SEQ ID NO 63
<211> LENGTH: 120
<212> TYPE: PRT
<213> ORGANISM: Homo sapiens

<400> SEQUENCE: 63

Ser Pro Tyr Lys Leu Asn Leu Val Ala Thr Pro Leu Phe Leu Lys Pro
  1               5                  10                  15

Gly Ile Pro Tyr Pro Ile Lys Val Gln Val Lys Asp Ser Leu Asp Gln
             20                  25                  30

Leu Val Gly Gly Val Pro Val Thr Leu Asn Ala Gln Thr Ile Asp Val
         35                  40                  45

Asn Gln Glu Thr Ser Asp Leu Asp Pro Ser Lys Ser Val Thr Arg Val
     50                  55                  60

Asp Asp Gly Val Ala Ser Phe Val Leu Asn Leu Pro Ser Gly Val Thr
 65                  70                  75                  80

Val Leu Glu Phe Asn Val Lys Thr Asp Ala Pro Asp Leu Pro Glu Glu
                 85                  90                  95

Asn Gln Ala Arg Glu Gly Tyr Arg Ala Ile Ala Tyr Ser Ser Leu Ser
            100                 105                 110

Gln Ser Tyr Leu Tyr Ile Asp Trp
        115                 120

<210> SEQ ID NO 64
<211> LENGTH: 366
<212> TYPE: DNA
<213> ORGANISM: Homo sapiens

<400> SEQUENCE: 64
gaggtgcagc tggtggagtc tggcggcgga ctggtgcagc ctggcggaag cttgcggctg      60
tcctgcgccg cctccggatt ctccttcagt ggcaggtact ggatacaatg ggtgcggcag     120
gcccctggca agggcctcga gtgggtggcc tctgtgtggc ctggtattac tggtgacact     180
aactacgcga actgggcgaa aggccggttc accatctccc gggacgactc caagaacacc     240
ctgtacctgc agatgaactc cctgcgggcc gaggacaccg ccgtgtacta ctgcgccaga     300
gaacctgttg cctggggtgg cggcttggac ttgtggggcc agggcacact agtgaccgtg     360
tcctcc                                                                366

<210> SEQ ID NO 65
<211> LENGTH: 366
<212> TYPE: DNA
<213> ORGANISM: Homo sapiens

<400> SEQUENCE: 65
gaggtgcagc tggtggagtc tggcggcgga ctggtgcagc ctggcggaag cttgcggctg      60
tcctgcgccg cctccggatt ctccttcagt ggcaggtact ggatacaatg ggtgcggcag     120
gcccctggca agggcctcga gtgggtggcc agtggttggc gggggcgac tggtgacact      180 aactacgcga actgggcgaa aggccggttc accatctccc gggacgactc caagaacacc     240
ctgtacctgc agatgaactc cctgcgggcc gaggacaccg ccgtgtacta ctgcgccaga     300
```

```
gaacctgttg cctggggtgg cggcttggac ttgtggggcc agggcacact agtgaccgtg    360
tcctcc                                                              366

<210> SEQ ID NO 66
<211> LENGTH: 366
<212> TYPE: DNA
<213> ORGANISM: Homo sapiens

<400> SEQUENCE: 66
gaggtgcagc tggtggagtc tggcggcgga ctggtgcagc ctggcggaag cttgcggctg    60
tcctgcgccg cctccggatt ctccttcagt ggcaggtact ggatacaatg ggtgcggcag   120
gcccctggca agggcctcga gtgggtggcc agttctagtt tgcgggggac tggtgacact   180
aactacgcga actgggcgaa aggccggttc accatctccc gggacgactc caagaacacc   240
ctgtacctgc agatgaactc cctgcgggcc gaggacaccg ccgtgtacta ctgcgccaga   300
gaacctgttg cctggggtgg cggcttggac ttgtggggcc agggcacact agtgaccgtg   360
tcctcc                                                              366

<210> SEQ ID NO 67
<211> LENGTH: 366
<212> TYPE: DNA
<213> ORGANISM: Homo sapiens

<400> SEQUENCE: 67
gaggtgcagc tggtggagtc tggcggcgga ctggtgcagc ctggcggaag cttgcggctg    60
tcctgcgccg cctccggatt ctccttcagt ggcaggtact ggatacaatg ggtgcggcag   120
gcccctggca agggcctcga gtgggtggcc tcggtgtggc cggggtttac tggtgacact   180
aactacgcga actgggcgaa aggccggttc accatctccc gggacgactc caagaacacc   240
ctgtacctgc agatgaactc cctgcgggcc gaggacaccg ccgtgtacta ctgcgccaga   300
gaacctgttg cctggggtgg cggcttggac ttgtggggcc agggcacact agtgaccgtg   360
tcctcc                                                              366

<210> SEQ ID NO 68
<211> LENGTH: 366
<212> TYPE: DNA
<213> ORGANISM: Homo sapiens

<400> SEQUENCE: 68
gaggtgcagc tggtggagtc tggcggcgga ctggtgcagc ctggcggaag cttgcggctg    60
tcctgcgccg cctccggatt ctccctcagt ggcaggtact ggatacaatg ggtgcggcag   120
gcccctggca agggcctcga gtgggtggcc agtggttggc cggggcgac tggtgacact    180 aactacgcga actgggcgaa aggccggttc accatctccc gggacgactc caagaacacc   240
ctgtacctgc agatgaactc cctgcgggcc gaggacaccg ccgtgtacta ctgcgccaga   300
gaacctgttg cctggggtgg cggcttggac ttgtggggcc agggcacact agtgaccgtg   360
tcctcc                                                              366

<210> SEQ ID NO 69
<211> LENGTH: 366
<212> TYPE: DNA
<213> ORGANISM: Homo sapiens

<400> SEQUENCE: 69
```

```
gaggtgcagc tggtggagtc tgScggcgga ctggtgcagc ctggcggaag cttgcggctg    60
tcctgcgccg cctccggatt ctccctcagt ggcaggtact ggatacaatg ggtgcggcag   120
gccccTGGCA agggcctcga gtgggtggcc tcggtgtggc cggggtttac tggtgacact   180
aactacgcga actgggcgaa aggccggttc accatctccc gggacgactc caagaacacc   240
ctgtacctgc agatgaactc cctgcgggcc gaggacaccg ccgtgtacta ctgcgccaga   300
gaacctgttg cctggggtgg cggcttggac ttgtggggcc agggcacact agtgaccgtg   360
tcctcc                                                              366
```

<210> SEQ ID NO 70
<211> LENGTH: 330
<212> TYPE: DNA
<213> ORGANISM: Homo sapiens

<400> SEQUENCE: 70

```
gacatccaga tgacccagtc cccctcctcg ctgagcgcct ccgtgggcga ccgggtgacc    60
atcacctgcc aggccagtca gagcattaac aaccaactat cctggtatca gcagaagcct   120
ggcaaggcgc ctaagctgct gatctactat gcatccactc tggcatctgg cgtgccttcc   180
cggttctccg gatccggctc cggcaccgac ttcaccctga ccatctcctc cctgcaacct   240
gaggacttcg ccacctacta ctgccaaggc agttattata gtggtggttg ggactatggt   300
ttcggccagg gtaccaaggt ggagatcaag                                    330
```

<210> SEQ ID NO 71
<211> LENGTH: 38
<212> TYPE: DNA
<213> ORGANISM: Artificial Sequence
<220> FEATURE:
<223> OTHER INFORMATION: Vk 5' Sense Primers - RSCVK1

<400> SEQUENCE: 71

```
gggcccaggc ggccgagctc gtgmtgaccc agactcca                           38
```

<210> SEQ ID NO 72
<211> LENGTH: 38
<212> TYPE: DNA
<213> ORGANISM: Artificial Sequence
<220> FEATURE:
<223> OTHER INFORMATION: Vk 5' Sense Primers - RSCVK2

<400> SEQUENCE: 72

```
gggcccaggc ggccgagctc gatmtgaccc agactcca                           38
```

<210> SEQ ID NO 73
<211> LENGTH: 38
<212> TYPE: DNA
<213> ORGANISM: Artificial Sequence
<220> FEATURE:
<223> OTHER INFORMATION: Vk 5' Sense Primers - RSCVK3

<400> SEQUENCE: 73

```
gggcccaggc ggccgagctc gtgatgaccc agactgaa                           38
```

<210> SEQ ID NO 74
<211> LENGTH: 75
<212> TYPE: DNA
<213> ORGANISM: Artificial Sequence
<220> FEATURE:
<223> OTHER INFORMATION: Vk 3' Reverse Primers, LongLinker - RKB9J1o-BL

<400> SEQUENCE: 74
ggaagatcta gaggaaccac ccccaccacc gcccgagcca ccgccaccag aggataggat    60
ctccagctcg gtccc    75

<210> SEQ ID NO 75
<211> LENGTH: 75
<212> TYPE: DNA
<213> ORGANISM: Artificial Sequence
<220> FEATURE:
<223> OTHER INFORMATION: Vk 3' Reverse Primers, LongLinker - RKB9Jo-BL

<400> SEQUENCE: 75
ggaagatcta gaggaaccac ccccaccacc gcccgagcca ccgccaccag aggataggat    60
ctccagctcg gtccc    75

<210> SEQ ID NO 76
<211> LENGTH: 75
<212> TYPE: DNA
<213> ORGANISM: Artificial Sequence
<220> FEATURE:
<223> OTHER INFORMATION: Vk 3' Reverse Primers, LongLinker - RKB42Jo-BL

<400> SEQUENCE: 76
ggaagatcta gaggaaccac ccccaccacc gcccgagcca ccgccaccag aggatttgac    60
saccacctcg gtccc    75

<210> SEQ ID NO 77
<211> LENGTH: 40
<212> TYPE: DNA
<213> ORGANISM: Artificial Sequence
<220> FEATURE:
<223> OTHER INFORMATION: V lamda 5'Sense Primer - RSC lamda 1

<400> SEQUENCE: 77
gggcccaggc ggccgagctc gtgctgactc agtcgccctc    40

<210> SEQ ID NO 78
<211> LENGTH: 78
<212> TYPE: DNA
<213> ORGANISM: Artificial Sequence
<220> FEATURE:
<223> OTHER INFORMATION: V lamda 3'Reverse Primer, LongLinker - RJ lamda
      o-BL

<400> SEQUENCE: 78
ggaagatcta gaggaaccac ccccaccacc gcccgagcca ccgccaccag aggagcctgt    60
gacggtcagc tgggtccc    78

<210> SEQ ID NO 79
<211> LENGTH: 42
<212> TYPE: DNA
<213> ORGANISM: Artificial Sequence
<220> FEATURE:
<223> OTHER INFORMATION: VH5'Sense Primers - RSCVH1

<400> SEQUENCE: 79
ggtggttcct ctagatcttc ccagtcggtg gaggagtccr gg    42

<210> SEQ ID NO 80
<211> LENGTH: 42
<212> TYPE: DNA
<213> ORGANISM: Artificial Sequence
<220> FEATURE:
<223> OTHER INFORMATION: VH5'Sense Primers - RSCVH2

<400> SEQUENCE: 80
ggtggttcct ctagatcttc ccagtcggtg aaggagtccg ag                                 42

<210> SEQ ID NO 81
<211> LENGTH: 42
<212> TYPE: DNA
<213> ORGANISM: Artificial Sequence
<220> FEATURE:
<223> OTHER INFORMATION: VH5'Sense Primers - RSCVH3

<400> SEQUENCE: 81
ggtggttcct ctagatcttc ccagtcgytg gaggagtccg gg                                 42

<210> SEQ ID NO 82
<211> LENGTH: 44
<212> TYPE: DNA
<213> ORGANISM: Artificial Sequence
<220> FEATURE:
<223> OTHER INFORMATION: VH5'Sense Primers - RSCVH4

<400> SEQUENCE: 82
ggtggttcct ctagatcttc ccagsagcag ctgrtggagt ccgg                               44

<210> SEQ ID NO 83
<211> LENGTH: 46
<212> TYPE: DNA
<213> ORGANISM: Artificial Sequence
<220> FEATURE:
<223> OTHER INFORMATION: VH3'Reverse Primers -RSCG-B

<400> SEQUENCE: 83
cctggccggc ctggccacta gtgactgayg gagccttagg ttgccc                             46

<210> SEQ ID NO 84
<211> LENGTH: 41
<212> TYPE: DNA
<213> ORGANISM: Artificial Sequence
<220> FEATURE:
<223> OTHER INFORMATION: Overlap Extension Primers - RSC-F (sense)

<400> SEQUENCE: 84
gaggaggagg aggaggaggc ggggcccagg cggccgagct c                                  41

<210> SEQ ID NO 85
<211> LENGTH: 41
<212> TYPE: DNA
<213> ORGANISM: Artificial Sequence
<220> FEATURE:
<223> OTHER INFORMATION: Overlap Extension Primers - RSC-B (reverse)

<400> SEQUENCE: 85
gaggaggagg aggaggagcc tggccggcct ggccactagt g                                  41

<210> SEQ ID NO 86
<211> LENGTH: 38
<212> TYPE: DNA
<213> ORGANISM: Artificial Sequence
<220> FEATURE:
<223> OTHER INFORMATION: V lamda Primers - CSCVK (sense)

<400> SEQUENCE: 86
gtggcccagg cggccctgac tcagccgtcc tcggtgtc                                      38

<210> SEQ ID NO 87

```
<211> LENGTH: 34
<212> TYPE: DNA
<213> ORGANISM: Artificial Sequence
<220> FEATURE:
<223> OTHER INFORMATION: V lamda Primers - CKJo-B (reverse)

<400> SEQUENCE: 87
ggaagatcta gaggactgac ctaggacggt cagg                                   34

<210> SEQ ID NO 88
<211> LENGTH: 72
<212> TYPE: DNA
<213> ORGANISM: Artificial Sequence
<220> FEATURE:
<223> OTHER INFORMATION: VHPrimers - CSCVHo-FL (sense)

<400> SEQUENCE: 88
ggtcagtcct ctagatcttc cggcggtggt ggcagctccg gtggtggcgg ttccgccgtg        60
acgttggacg ag                                                            72

<210> SEQ ID NO 89
<211> LENGTH: 44
<212> TYPE: DNA
<213> ORGANISM: Artificial Sequence
<220> FEATURE:
<223> OTHER INFORMATION: VHPrimers - CSCG-B (reverse)

<400> SEQUENCE: 89
ctggccggcc tgccactag tggaggagac gatgacttcg gtcc                          44

<210> SEQ ID NO 90
<211> LENGTH: 42
<212> TYPE: DNA
<213> ORGANISM: Artificial Sequence
<220> FEATURE:
<223> OTHER INFORMATION: Overlap Extension Primers  -  CSC-F (sense)

<400> SEQUENCE: 90
gaggaggagg aggaggaggt ggcccaggcg gccctgactc ag                           42

<210> SEQ ID NO 91
<211> LENGTH: 47
<212> TYPE: DNA
<213> ORGANISM: Artificial Sequence
<220> FEATURE:
<223> OTHER INFORMATION: Overlap Extension Primers  -  CSC-B (reverse)

<400> SEQUENCE: 91
gaggaggagg aggaggagga gctggccggc ctggccacta gtggagg                      47

<210> SEQ ID NO 92
<211> LENGTH: 36
<212> TYPE: DNA
<213> ORGANISM: Artificial Sequence
<220> FEATURE:
<223> OTHER INFORMATION: Forward  primers  -  MG1-F

<400> SEQUENCE: 92
ggcccaggcg gccatgggcc ttttgggaat actttg                                  36

<210> SEQ ID NO 93
<211> LENGTH: 36
<212> TYPE: DNA
<213> ORGANISM: Artificial Sequence
<220> FEATURE:
<223> OTHER INFORMATION: Forward  primers  -  MG2-F
```

```
<400> SEQUENCE: 93
ggcccaggcg gccaatggat ttctcttcat tcatac                              36

<210> SEQ ID NO 94
<211> LENGTH: 34
<212> TYPE: DNA
<213> ORGANISM: Artificial Sequence
<220> FEATURE:
<223> OTHER INFORMATION: Forward primers - MG3-F

<400> SEQUENCE: 94
ggcccaggcg gccccacatt tttctgtctc aatc                                34

<210> SEQ ID NO 95
<211> LENGTH: 34
<212> TYPE: DNA
<213> ORGANISM: Artificial Sequence
<220> FEATURE:
<223> OTHER INFORMATION: Forward primers - MG4-F

<400> SEQUENCE: 95
ggcccaggcg gcctctccct acaaactgaa tttg                                34

<210> SEQ ID NO 96
<211> LENGTH: 34
<212> TYPE: DNA
<213> ORGANISM: Artificial Sequence
<220> FEATURE:
<223> OTHER INFORMATION: Forward primers- MG5-F

<400> SEQUENCE: 96
ggcccaggcg gccactgata accataaggc tttg                                34

<210> SEQ ID NO 97
<211> LENGTH: 30
<212> TYPE: DNA
<213> ORGANISM: Artificial Sequence
<220> FEATURE:
<223> OTHER INFORMATION: Forward primers- Linker-F

<400> SEQUENCE: 97
ggcccaggcg gcctcctggg tggcattagc                                     30

<210> SEQ ID NO 98
<211> LENGTH: 34
<212> TYPE: DNA
<213> ORGANISM: Artificial Sequence
<220> FEATURE:
<223> OTHER INFORMATION: Reverse primers - MG1-R

<400> SEQUENCE: 98
ggccggcctg gccgtcatag gttattggca ttct                                34

<210> SEQ ID NO 99
<211> LENGTH: 34
<212> TYPE: DNA
<213> ORGANISM: Artificial Sequence
<220> FEATURE:
<223> OTHER INFORMATION: Reverse primers - MG2-R

<400> SEQUENCE: 99
ggccggcctg gcccaagaca tattctttaa cttc                                34

<210> SEQ ID NO 100
```

<211> LENGTH: 33
<212> TYPE: DNA
<213> ORGANISM: Artificial Sequence
<220> FEATURE:
<223> OTHER INFORMATION: Reverse primers - MG3-R

<400> SEQUENCE: 100
ggccggcctg gccgaggaca tatttgatgc cag          33

<210> SEQ ID NO 101
<211> LENGTH: 37
<212> TYPE: DNA
<213> ORGANISM: Artificial Sequence
<220> FEATURE:
<223> OTHER INFORMATION: Reverse primers - MG4-R

<400> SEQUENCE: 101
ggccggcctg gccccaatca atataaaggt aactttg      37

<210> SEQ ID NO 102
<211> LENGTH: 35
<212> TYPE: DNA
<213> ORGANISM: Artificial Sequence
<220> FEATURE:
<223> OTHER INFORMATION: Reverse primers - MG5-R

<400> SEQUENCE: 102
ggccggcctg gccatccatt ccagttgcca tatta        35

<210> SEQ ID NO 103
<211> LENGTH: 34
<212> TYPE: DNA
<213> ORGANISM: Artificial Sequence
<220> FEATURE:
<223> OTHER INFORMATION: Reverse primers - Linker-R

<400> SEQUENCE: 103
ggccggcctg gccgagaatt tctttacaag gttc         34

<210> SEQ ID NO 104
<211> LENGTH: 34
<212> TYPE: DNA
<213> ORGANISM: Artificial Sequence
<220> FEATURE:
<223> OTHER INFORMATION: Forward primers - hMG4-F

<400> SEQUENCE: 104
ggcccaggcg gcctctccct acaaactgaa tttg         34

<210> SEQ ID NO 105
<211> LENGTH: 32
<212> TYPE: DNA
<213> ORGANISM: Artificial Sequence
<220> FEATURE:
<223> OTHER INFORMATION: Forward primers- d332-348_F

<400> SEQUENCE: 105
ggcccaggcg gccattccat atcccatcaa gg           32

<210> SEQ ID NO 106
<211> LENGTH: 34
<212> TYPE: DNA
<213> ORGANISM: Artificial Sequence
<220> FEATURE:
<223> OTHER INFORMATION: Forward primers- d332-378-F

<400> SEQUENCE: 106
ggcccaggcg gccgtaaacc aagagacatc tgac        34

<210> SEQ ID NO 107
<211> LENGTH: 32
<212> TYPE: DNA
<213> ORGANISM: Artificial Sequence
<220> FEATURE:
<223> OTHER INFORMATION: Forward primers - d332-396-F

<400> SEQUENCE: 107
ggcccaggcg gccgatggag tagcttcctt tg        32

<210> SEQ ID NO 108
<211> LENGTH: 31
<212> TYPE: DNA
<213> ORGANISM: Artificial Sequence
<220> FEATURE:
<223> OTHER INFORMATION: Forward primers - d332-424-F

<400> SEQUENCE: 108
ggcccaggcg gccccagaag aaaatcaggc c        31

<210> SEQ ID NO 109
<211> LENGTH: 37
<212> TYPE: DNA
<213> ORGANISM: Artificial Sequence
<220> FEATURE:
<223> OTHER INFORMATION: Reverse primers - hMG4-R

<400> SEQUENCE: 109
ggccggcctg gccccaatca atataaggt aactttg        37

<210> SEQ ID NO 110
<211> LENGTH: 86
<212> TYPE: DNA
<213> ORGANISM: Artificial Sequence
<220> FEATURE:
<223> OTHER INFORMATION: Construction of hMG4-m332-348 - m332-348F

<400> SEQUENCE: 110
ggcccaggcg gcctctccct acacactgaa tttggtcgct actcctcttt tcgtgaagcc        60
cgggattcca tatcccatca aggtgc        86

<210> SEQ ID NO 111
<211> LENGTH: 34
<212> TYPE: DNA
<213> ORGANISM: Artificial Sequence
<220> FEATURE:
<223> OTHER INFORMATION: Construction of hMG4-m332-348 - hMG4_R

<400> SEQUENCE: 111
ggcccaggcg gcctctccct acaaactgaa tttg        34

<210> SEQ ID NO 112
<211> LENGTH: 22
<212> TYPE: DNA
<213> ORGANISM: Artificial Sequence
<220> FEATURE:
<223> OTHER INFORMATION: Forward primer - mMG4_F (Mouse MG4 N-terminal)

<400> SEQUENCE: 112
tctccctaca cactgaattt gg        22

<210> SEQ ID NO 113

```
<211> LENGTH: 28
<212> TYPE: DNA
<213> ORGANISM: Artificial Sequence
<220> FEATURE:
<223> OTHER INFORMATION: Reverse primer - m332-359_R (Mouse MG4 N-
      terminal)

<400> SEQUENCE: 113
gtcaagcgaa tctttaacct gtgccttg                                         28

<210> SEQ ID NO 114
<211> LENGTH: 27
<212> TYPE: DNA
<213> ORGANISM: Artificial Sequence
<220> FEATURE:
<223> OTHER INFORMATION: Reverse primer - m332-368_R (Mouse MG4 N-
      terminal)

<400> SEQUENCE: 114
tgttactggg acccctccta ccgcctg                                          27

<210> SEQ ID NO 115
<211> LENGTH: 28
<212> TYPE: DNA
<213> ORGANISM: Artificial Sequence
<220> FEATURE:
<223> OTHER INFORMATION: Reverse primer - m332-378_R (Mouse MG4 N-
      terminal)

<400> SEQUENCE: 115
ttggtttaca tcgactgttt gtgccatc                                         28

<210> SEQ ID NO 116
<211> LENGTH: 30
<212> TYPE: DNA
<213> ORGANISM: Artificial Sequence
<220> FEATURE:
<223> OTHER INFORMATION: Reverse primer - m332-385_R (Mouse MG4 N-
      terminal)

<400> SEQUENCE: 116
tggatccaag tcagatgtct cttgattcac                                       30

<210> SEQ ID NO 117
<211> LENGTH: 28
<212> TYPE: DNA
<213> ORGANISM: Artificial Sequence
<220> FEATURE:
<223> OTHER INFORMATION: Reverse primer - m332-392_R (Mouse MG4 N-
      terminal)

<400> SEQUENCE: 117
aacacgtgtg atgctcctct ttgtttcc                                         28

<210> SEQ ID NO 118
<211> LENGTH: 28
<212> TYPE: DNA
<213> ORGANISM: Artificial Sequence
<220> FEATURE:
<223> OTHER INFORMATION: Reverse primer - m332-398_R (Mouse MG4 N-
      terminal)

<400> SEQUENCE: 118
ggaagctact ccatcagtgt catgagtg                                         28

<210> SEQ ID NO 119
<211> LENGTH: 28
```

```
<212> TYPE: DNA
<213> ORGANISM: Artificial Sequence
<220> FEATURE:
<223> OTHER INFORMATION: Reverse primer - m332-409_R (Mouse MG4 N-
      terminal)

<400> SEQUENCE: 119
caccgtcaca tttgatggga ggttcagc                                           28

<210> SEQ ID NO 120
<211> LENGTH: 28
<212> TYPE: DNA
<213> ORGANISM: Artificial Sequence
<220> FEATURE:
<223> OTHER INFORMATION: Forward primer - m332-359_F (Human MG4 C-
      terminal)

<400> SEQUENCE: 120
gttaaagatt cgcttgacca gttggtag                                           28

<210> SEQ ID NO 121
<211> LENGTH: 28
<212> TYPE: DNA
<213> ORGANISM: Artificial Sequence
<220> FEATURE:
<223> OTHER INFORMATION: Forward primer - m332-368_F (Human MG4 C-
      terminal)

<400> SEQUENCE: 121
ggaggggtcc cagtaacact gaatgcac                                           28

<210> SEQ ID NO 122
<211> LENGTH: 30
<212> TYPE: DNA
<213> ORGANISM: Artificial Sequence
<220> FEATURE:
<223> OTHER INFORMATION: Forward primer -m332-378_F (Human MG4 C-
      terminal)

<400> SEQUENCE: 122
acagtcgatg taaaccaaga gacatctgac                                         30

<210> SEQ ID NO 123
<211> LENGTH: 29
<212> TYPE: DNA
<213> ORGANISM: Artificial Sequence
<220> FEATURE:
<223> OTHER INFORMATION: Forward primer -m332-385_F (Human MG4 C-
      terminal)

<400> SEQUENCE: 123
acatctgact tggatccaag caaaagtgt                                          29

<210> SEQ ID NO 124
<211> LENGTH: 30
<212> TYPE: DNA
<213> ORGANISM: Artificial Sequence
<220> FEATURE:
<223> OTHER INFORMATION: Forward primer -m332-392_F (Human MG4 C-
      terminal)

<400> SEQUENCE: 124
aggagcatca cacgtgttga tgatggagta                                         30

<210> SEQ ID NO 125
<211> LENGTH: 31
<212> TYPE: DNA
```

```
<213> ORGANISM: Artificial Sequence
<220> FEATURE:
<223> OTHER INFORMATION: Forward primer -m332-398_F (Human MG4 C-
      terminal)

<400> SEQUENCE: 125
actgatggag tagcttcctt tgtgcttaat c                                    31

<210> SEQ ID NO 126
<211> LENGTH: 28
<212> TYPE: DNA
<213> ORGANISM: Artificial Sequence
<220> FEATURE:
<223> OTHER INFORMATION: Forward primer -m332-409_F (Human MG4 C-
      terminal)

<400> SEQUENCE: 126
ccatcaaatg tgacggtgct ggagttta                                        28

<210> SEQ ID NO 127
<211> LENGTH: 34
<212> TYPE: DNA
<213> ORGANISM: Artificial Sequence
<220> FEATURE:
<223> OTHER INFORMATION: Reverse primer - hMG4_R (Human MG4 C-terminal)

<400> SEQUENCE: 127
ggcccaggcg gcctctccct acaaactgaa tttg                                 34

<210> SEQ ID NO 128
<211> LENGTH: 82
<212> TYPE: DNA
<213> ORGANISM: Artificial Sequence
<220> FEATURE:
<223> OTHER INFORMATION: Construction of mMG4-h332-348   - h332-348_F

<400> SEQUENCE: 128
ggcccaggcg gcctctccct acaaactgaa tttggttgct actcctcttt tcctgaagcc     60
tgggattcca ttttccatca ag                                              82

<210> SEQ ID NO 129
<211> LENGTH: 20
<212> TYPE: DNA
<213> ORGANISM: Artificial Sequence
<220> FEATURE:
<223> OTHER INFORMATION: Construction of mMG4-h332-348   - mMG4_R

<400> SEQUENCE: 129
ccaagcgatg taaatgtaac                                                 20

<210> SEQ ID NO 130
<211> LENGTH: 34
<212> TYPE: DNA
<213> ORGANISM: Artificial Sequence
<220> FEATURE:
<223> OTHER INFORMATION: Forward primer -  hMG4-F (Human MG4 N-terminal)

<400> SEQUENCE: 130
ggcccaggcg gcctctccct acaaactgaa tttg                                 34

<210> SEQ ID NO 131
<211> LENGTH: 29
<212> TYPE: DNA
<213> ORGANISM: Artificial Sequence
<220> FEATURE:
<223> OTHER INFORMATION: Reverse primer -  h332-359_R (Human MG4 N-
``` terminal)

<400> SEQUENCE: 131
ctcgagtgaa tctttaacct gcaccttga                                        29

<210> SEQ ID NO 132
<211> LENGTH: 27
<212> TYPE: DNA
<213> ORGANISM: Artificial Sequence
<220> FEATURE:
<223> OTHER INFORMATION: Reverse primer - h332-368_R (Human MG4 N-
      terminal)

<400> SEQUENCE: 132
agttactggg actcctccta ccaactg                                          27

<210> SEQ ID NO 133
<211> LENGTH: 30
<212> TYPE: DNA
<213> ORGANISM: Artificial Sequence
<220> FEATURE:
<223> OTHER INFORMATION: Reverse primer - h332-378_R (Human MG4 N-
      terminal)

<400> SEQUENCE: 133
ttgattcaca tcaattgttt gtgcattcag                                       30

<210> SEQ ID NO 134
<211> LENGTH: 30
<212> TYPE: DNA
<213> ORGANISM: Artificial Sequence
<220> FEATURE:
<223> OTHER INFORMATION: Reverse primer - h332-385_R (Human MG4 N-
      terminal)

<400> SEQUENCE: 134
tgtttccaag tcagatgtct cttggtttac                                       30

<210> SEQ ID NO 135
<211> LENGTH: 29
<212> TYPE: DNA
<213> ORGANISM: Artificial Sequence
<220> FEATURE:
<223> OTHER INFORMATION: Reverse primer - h332-392_R (Human MG4 N-
      terminal)

<400> SEQUENCE: 135
gtcatgagtt acactttgc ttggatcca                                         29

<210> SEQ ID NO 136
<211> LENGTH: 30
<212> TYPE: DNA
<213> ORGANISM: Artificial Sequence
<220> FEATURE:
<223> OTHER INFORMATION: Reverse primer - h332-398_R (Human MG4 N-
      terminal)

<400> SEQUENCE: 136
cacagctact ccatcatcaa cacgtgttac                                       30

<210> SEQ ID NO 137
<211> LENGTH: 30
<212> TYPE: DNA
<213> ORGANISM: Artificial Sequence
<220> FEATURE:
<223> OTHER INFORMATION: Reverse primer - h332-409_R (Human MG4 N-
      terminal)

```
<400> SEQUENCE: 137
caccgtcact ccagatggga gattaagcac                                    30

<210> SEQ ID NO 138
<211> LENGTH: 26
<212> TYPE: DNA
<213> ORGANISM: Artificial Sequence
<220> FEATURE:
<223> OTHER INFORMATION: Forward primer -  h332-359_F (Mouse MG4 C-
      terminal)

<400> SEQUENCE: 138
gttaaagatt cactcgagca ggcggt                                        26

<210> SEQ ID NO 139
<211> LENGTH: 28
<212> TYPE: DNA
<213> ORGANISM: Artificial Sequence
<220> FEATURE:
<223> OTHER INFORMATION: Forward primer -  h332-368_F (Mouse MG4 C-
      terminal)

<400> SEQUENCE: 139
ggaggagtcc cagtaactct gatggcac                                      28

<210> SEQ ID NO 140
<211> LENGTH: 30
<212> TYPE: DNA
<213> ORGANISM: Artificial Sequence
<220> FEATURE:
<223> OTHER INFORMATION: Forward primer -  h332-378_F (Mouse MG4 C-
      terminal)

<400> SEQUENCE: 140
acaattgatg tgaatcaaga gacatctgac                                    30

<210> SEQ ID NO 141
<211> LENGTH: 30
<212> TYPE: DNA
<213> ORGANISM: Artificial Sequence
<220> FEATURE:
<223> OTHER INFORMATION: Forward primer -  h332-385_F (Mouse MG4 C-
      terminal)

<400> SEQUENCE: 141
acatctgact tggaaacaaa gaggagcatc                                    30

<210> SEQ ID NO 142
<211> LENGTH: 29
<212> TYPE: DNA
<213> ORGANISM: Artificial Sequence
<220> FEATURE:
<223> OTHER INFORMATION: Forward primer -  h332-392_F (Mouse MG4 C-
      terminal)

<400> SEQUENCE: 142
caaaagtgta actcatgaca ctgatggag                                     29

<210> SEQ ID NO 143
<211> LENGTH: 30
<212> TYPE: DNA
<213> ORGANISM: Artificial Sequence
<220> FEATURE:
<223> OTHER INFORMATION: Forward primer -  h332-398_F(Mouse MG4 C-
      terminal)
```

```
<400> SEQUENCE: 143
gatgatggag tagctgtgtt tgtgctgaac                                30

<210> SEQ ID NO 144
<211> LENGTH: 28
<212> TYPE: DNA
<213> ORGANISM: Artificial Sequence
<220> FEATURE:
<223> OTHER INFORMATION: Forward primer -   h332-409_F (Mouse MG4 C-
      terminal)

<400> SEQUENCE: 144
ccatctggag tgacggtgct aaagtttg                                  28

<210> SEQ ID NO 145
<211> LENGTH: 20
<212> TYPE: DNA
<213> ORGANISM: Artificial Sequence
<220> FEATURE:
<223> OTHER INFORMATION: Reverse primer -   mMG4_R (Mouse MG4 C-
      terminal)

<400> SEQUENCE: 145
ccaagcgatg taaatgtaac                                           20
```